(12) United States Patent
Valdez et al.

(10) Patent No.: US 11,517,391 B2
(45) Date of Patent: Dec. 6, 2022

(54) ANTI-MICROBIAL IV TUBING PROTECTION SYSTEM

(71) Applicant: I+D Device Solutions LLC, Corona, CA (US)

(72) Inventors: Desiree Valdez, Loma Linda, CA (US); Iris Geretschnig, Corona, CA (US); Gregory Tudryn, San Diego, CA (US)

(73) Assignee: I+D Device Solutions LLC, Corona, CA (US)

( * ) Notice: Subject to any disclaimer, the term of this patent is extended or adjusted under 35 U.S.C. 154(b) by 0 days.

(21) Appl. No.: 17/517,242

(22) Filed: Nov. 2, 2021

(65) Prior Publication Data
US 2022/0054217 A1 Feb. 24, 2022

Related U.S. Application Data

(63) Continuation-in-part of application No. PCT/US2021/043054, filed on Jul. 23, 2021.
(Continued)

(51) Int. Cl.
*A61B 90/00* (2016.01)
*A61M 39/08* (2006.01)
(Continued)

(52) U.S. Cl.
CPC .............. *A61B 90/08* (2016.02); *A61M 5/14* (2013.01); *A61M 39/08* (2013.01);
(Continued)

(58) Field of Classification Search
CPC ......... A61B 90/08; A61B 46/00; A61B 46/10; A61M 39/08; A61M 39/16; A61M 2039/087; A61M 2205/0205
See application file for complete search history.

(56) References Cited

U.S. PATENT DOCUMENTS 4,178,735 A 12/1979 Jackson
4,392,853 A * 7/1983 Muto ................... A61M 25/02
604/174
(Continued)

FOREIGN PATENT DOCUMENTS

CN 209 864 977 U 12/2019

OTHER PUBLICATIONS

"CareAline PICC Line Sleeve," Mar. 4, 2013 (see comment posted by Stacey on Mar. 4, 2013), CareAline Products, Retrieved Jun. 8, 2022, from <https://shop.carealine.com/carealine-picc-line-sleeve/?revpage=9%20#product-reviews>. (Year: 2013).*
(Continued)

*Primary Examiner* — Tasnim Mehjabin Ahmed
(74) *Attorney, Agent, or Firm* — Cooley LLP

(57) ABSTRACT

Embodiments described herein relate to encasements for protection of central lines, arterial lines, and/or intravenous (IV) lines from contaminants, and methods of making and using the same. In some embodiments, an encasement device can include a flexible sleeve that fits over a central line and protects the central line from contaminants. The flexible sleeve has a first open end and a second open end. A first closing element secures the first open end to a medical dressing and a second closing element secures the second open end in a closed position at a location distal to the first closing element. In some embodiments, the central line can include an intravenous (IV) catheter, a peripherally inserted central catheter (PICC) and/or a hemodialysis line. In some embodiments, the device can include a flap coupled to the flexible sleeve.

26 Claims, 23 Drawing Sheets

Related U.S. Application Data

(60) Provisional application No. 63/056,618, filed on Jul. 25, 2020.

(51) Int. Cl.
*A61M 39/16* (2006.01)
*A61M 5/14* (2006.01)
*A61M 39/10* (2006.01)

(52) U.S. Cl.
CPC ... *A61M 39/165* (2013.01); *A61M 2039/1066* (2013.01); *A61M 2205/0205* (2013.01)

(56) References Cited

U.S. PATENT DOCUMENTS

| | | | | |
|---|---|---|---|---|
| 5,539,162 | A * | 7/1996 | Tuttle | A61B 46/10 D24/134 |
| 5,665,073 | A | 9/1997 | Bulow et al. | |
| 6,749,601 | B2 * | 6/2004 | Chin | A61B 46/13 606/1 |
| 2004/0074501 | A1 | 4/2004 | Altman | |
| 2004/0077998 | A1 * | 4/2004 | Morris | A61M 5/14 604/93.01 |
| 2005/0211590 | A1 | 9/2005 | McLure et al. | |
| 2013/0012883 | A1 * | 1/2013 | Fitzgerald | A61M 39/08 604/179 |
| 2014/0088511 | A1 * | 3/2014 | Mullet | A61M 5/1418 604/164.08 |
| 2015/0257833 | A1 | 9/2015 | Dabel | |
| 2017/0367779 | A1 * | 12/2017 | Skroski | A61B 90/08 |
| 2019/0381305 | A1 | 12/2019 | Justus | |
| 2020/0324041 | A1 * | 10/2020 | Ervin | A61M 5/1418 |

OTHER PUBLICATIONS

Partial International Search Report dated Oct. 27, 2021 for International Application No. PCT/US2021/043054, 21 pages.

* cited by examiner

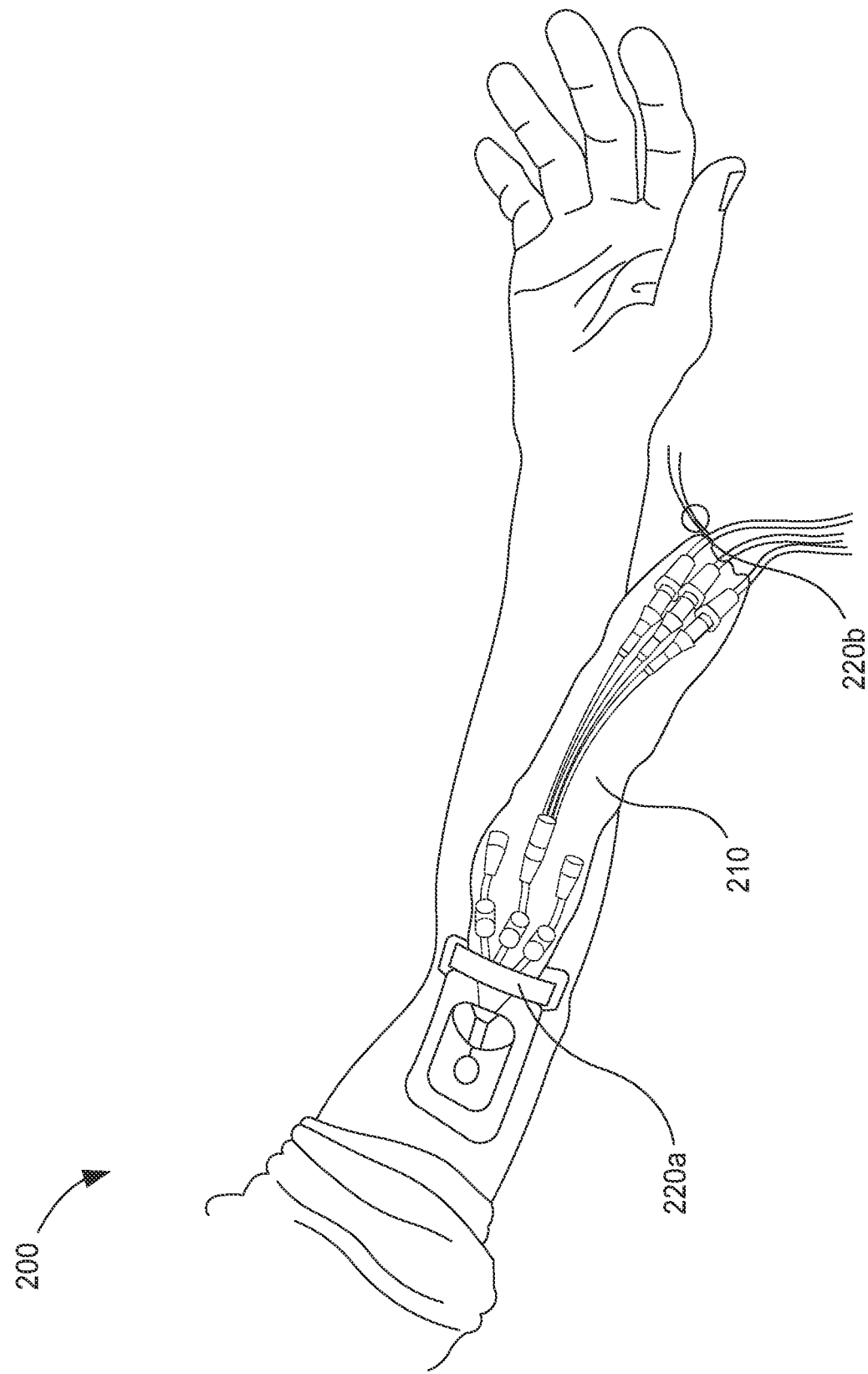

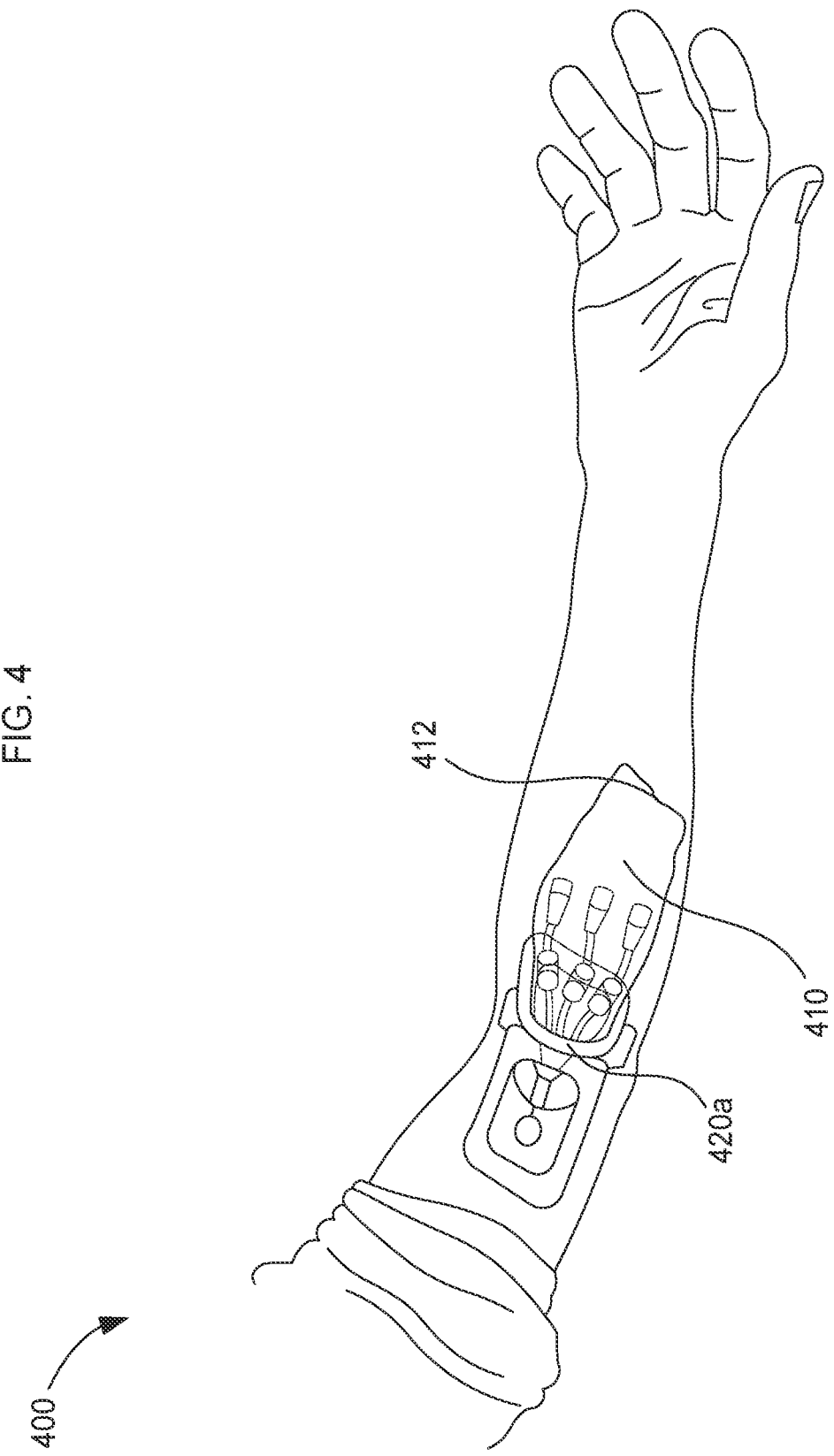

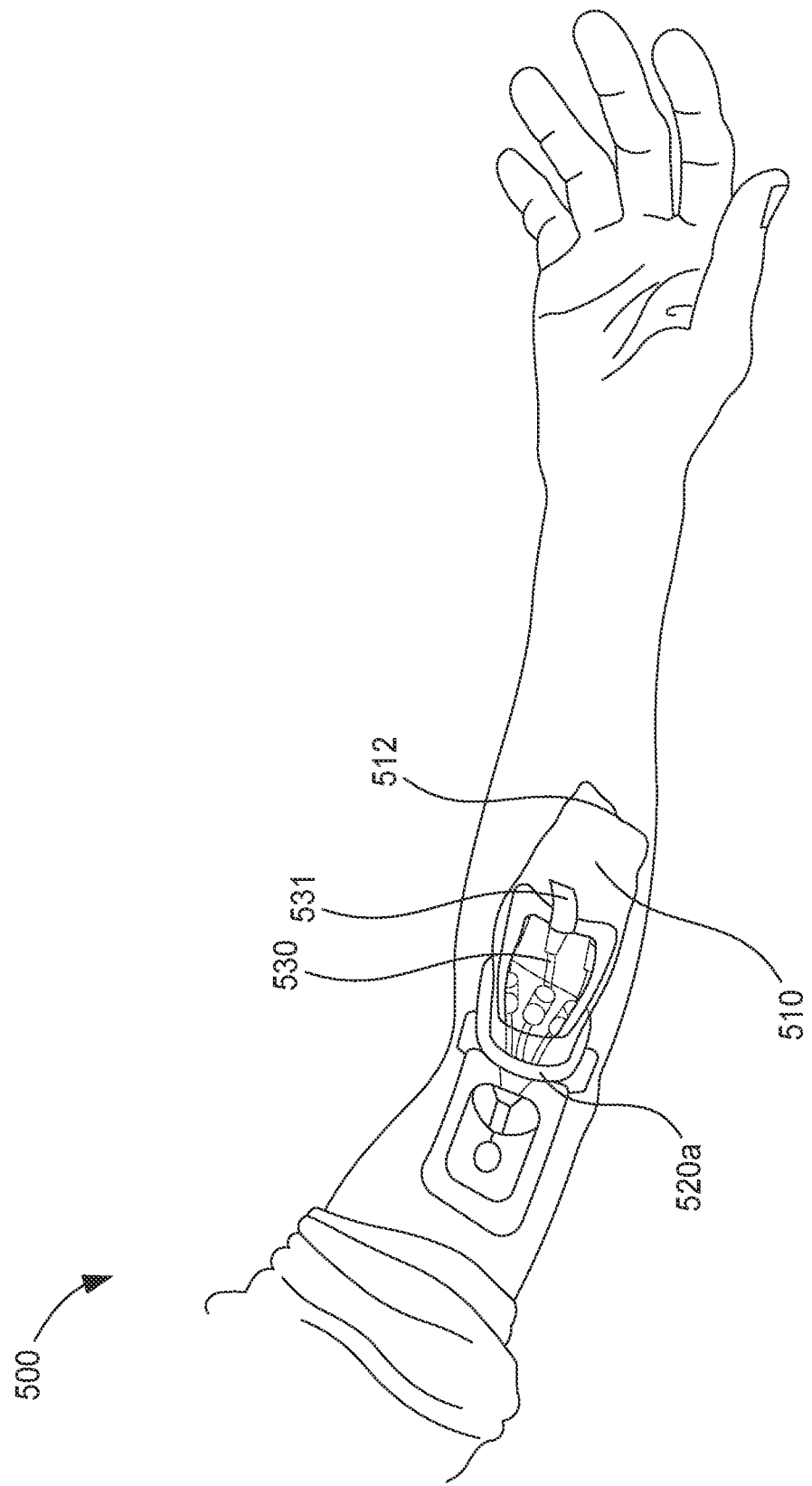

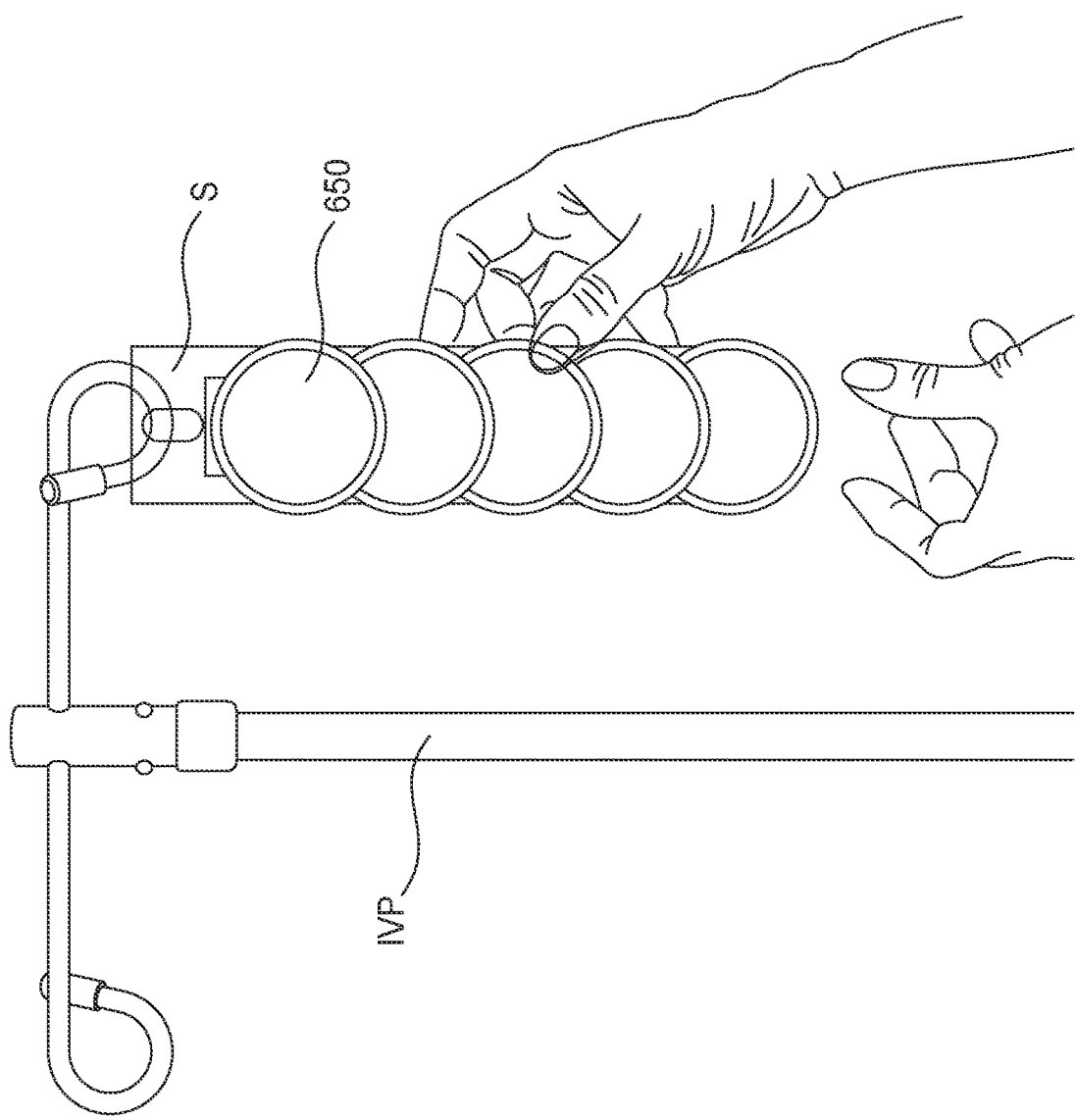
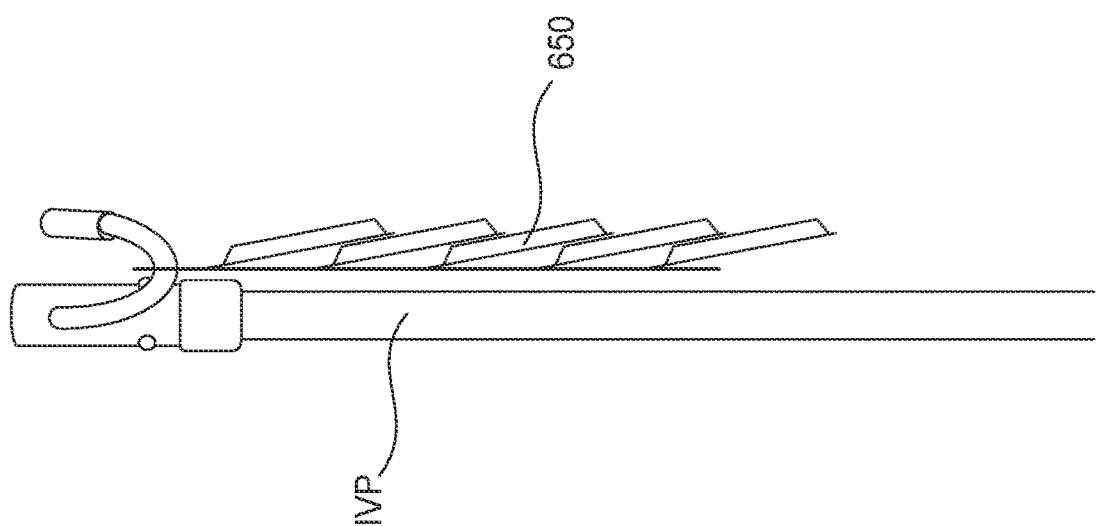

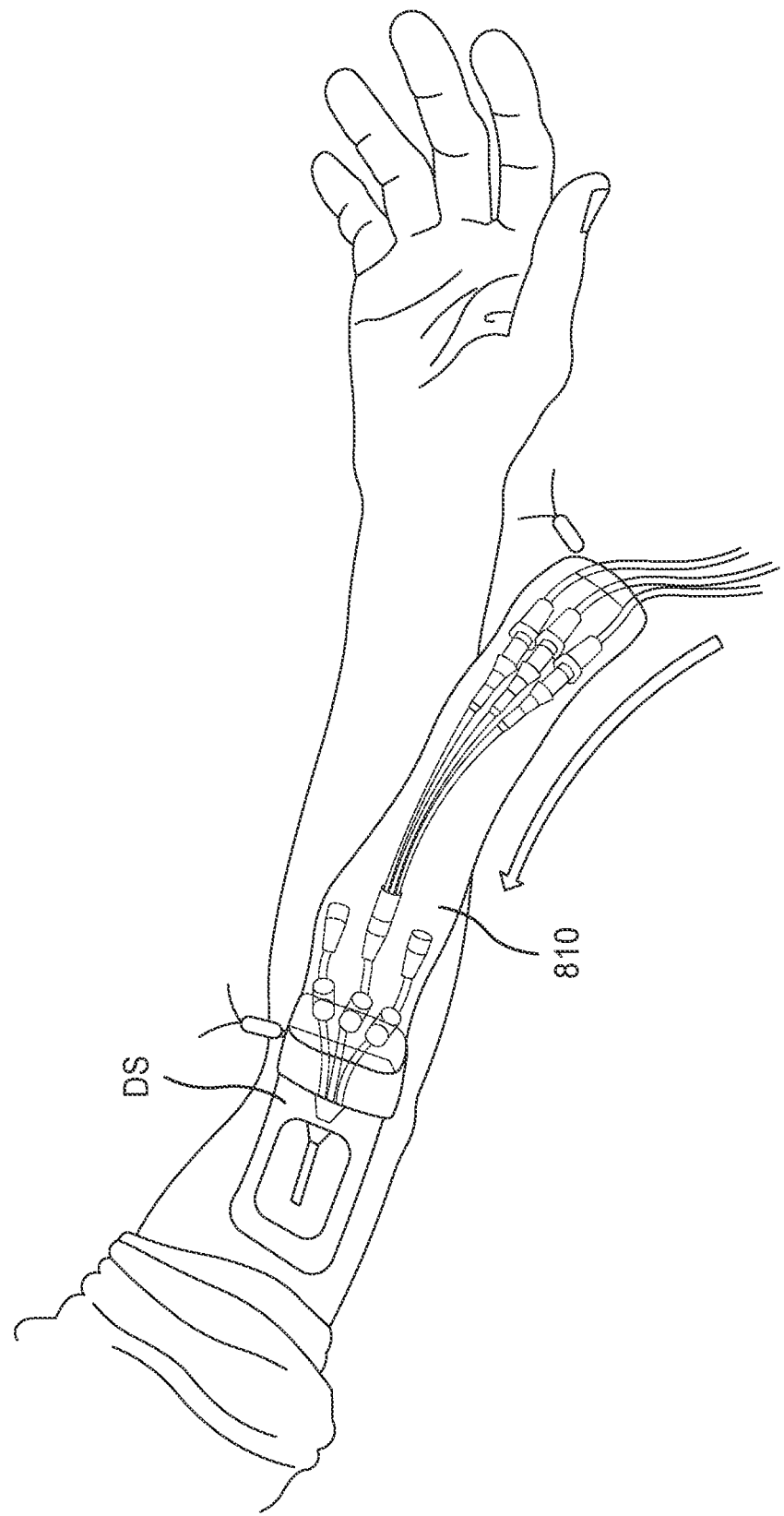

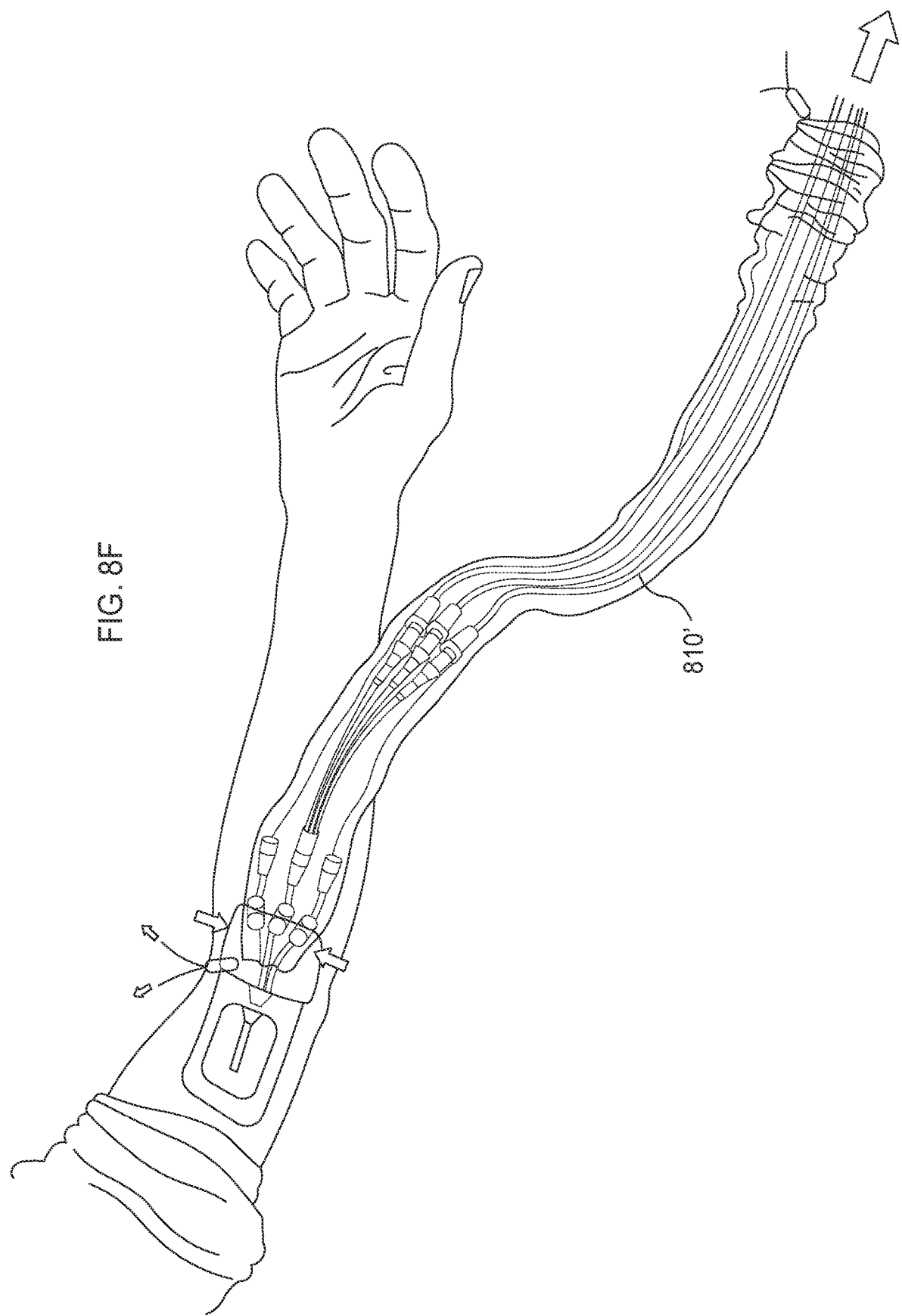

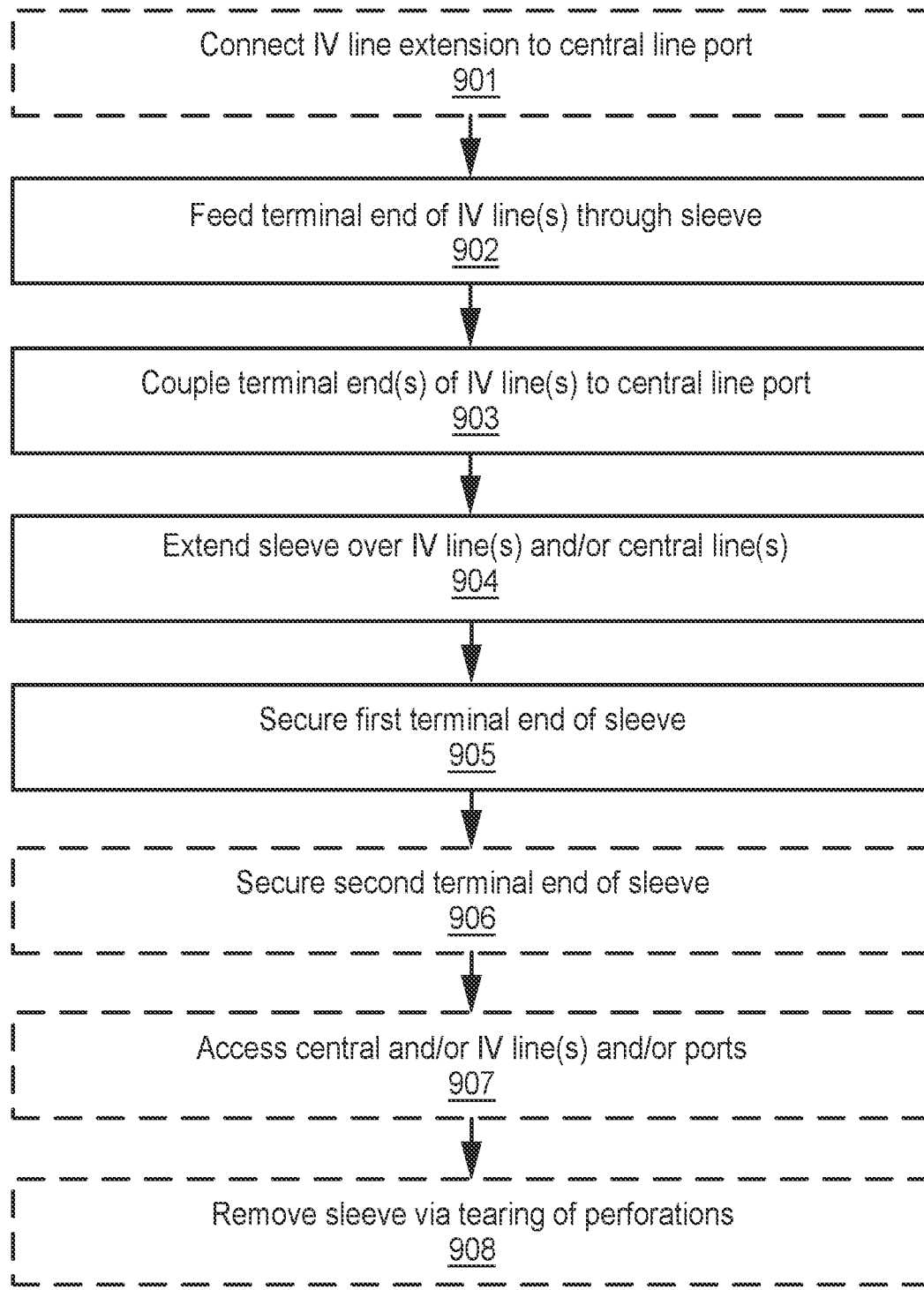

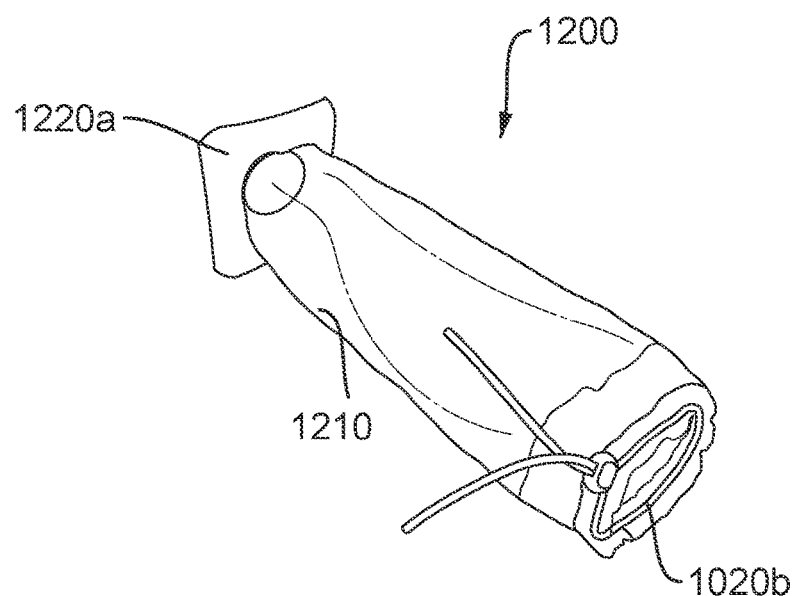
FIG. 12A
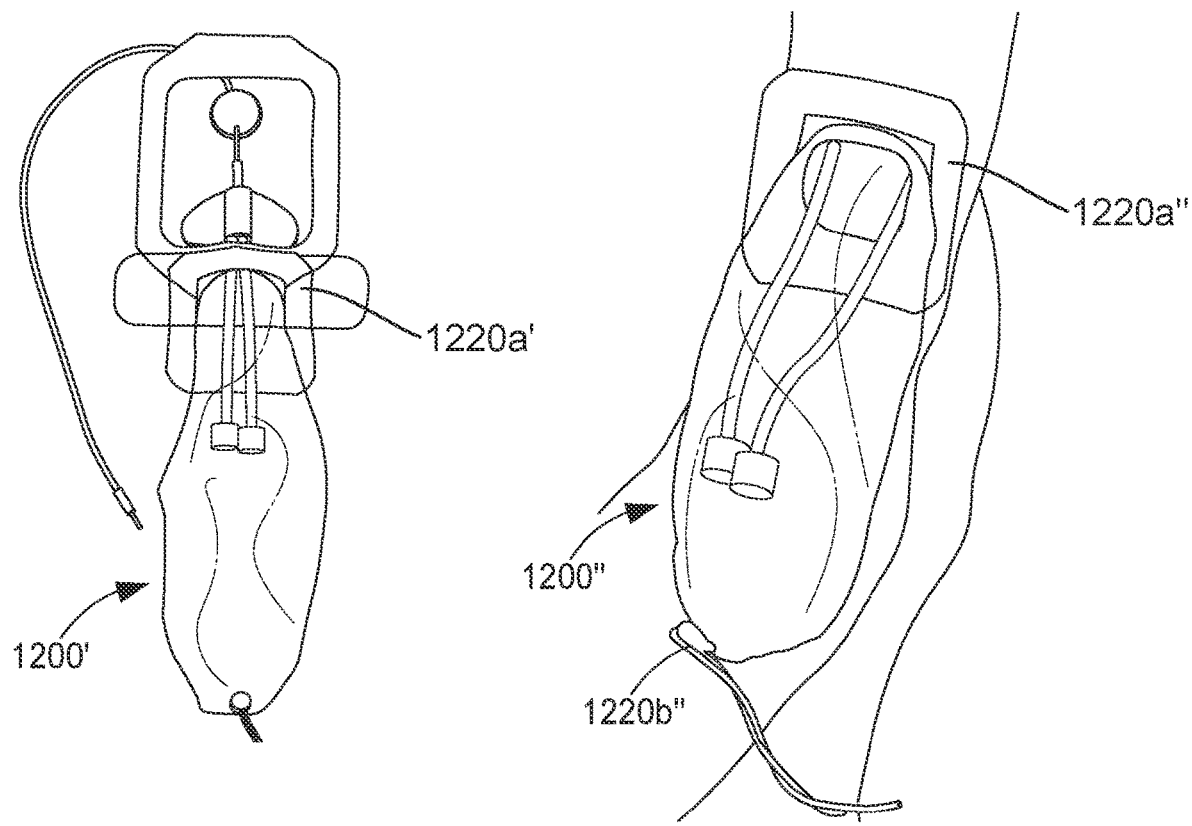
FIG. 12B
FIG. 12C

ANTI-MICROBIAL IV TUBING PROTECTION SYSTEM

CROSS-REFERENCE TO RELATED APPLICATIONS

This application is a continuation-in-part of International Patent Application No. PCT/US2021/043054, filed Jul. 23, 2021, and entitled "Anti-Microbial Tubing Protection System," which claims priority to and the benefit of U.S. Provisional Application No. 63/056,618, filed Jul. 25, 2020 and entitled "Anti-Microbial IV Tubing Protection System," the entire disclosures of which are hereby incorporated by reference herein in their entireties.

TECHNICAL FIELD

The present disclosure relates generally to tubing encasements or coverings, and methods of making and using the same, and more specifically, to protective coverings for intravenous (IV) tubing, catheter tubing, IV ports, IV connector sites or other types of tubing used in a medical setting.

BACKGROUND

Central line-associated bloodstream infections (CLABSI) are one of the most expensive healthcare associated infections (HAI) despite being highly preventable. CLABSI reduction can lower preventable morbidity and mortality as well as significantly decrease unnecessary healthcare costs. The Centers for Disease Control and Prevention (CDC) has made reducing HAIs a top priority, yet despite healthcare workers' adherence to CDC guidelines for CLABSI prevention, CLABSI rates continue to increase and have been exacerbated by the COVID-19 pandemic. CLABSI's are commonly caused by microbes such as bacteria, fungi, and viruses including, but not limited to *Staphylococci, Enterococci, Staph aureus, Klebsiella, Enterobacter, Pseudomonas, E. coli*, and *Candida* on medical equipment and/or lines, as well as patient's skin and surrounding surfaces. These microbes can migrate into the bloodstream via catheter sites and cause infections. Solutions are therefore needed that reduce the migration of such microbes near catheter sites.

SUMMARY

Embodiments described herein relate generally to encasements for protecting of central lines, IV lines, IV ports, and/or connection sites from contaminants, and methods of making and using the same. In some embodiments, an encasement device can include a flexible sleeve that fits over IV tubing, IV ports, and connection sites and protects from contaminants. The flexible sleeve has a first open end and a second open end. First and second closing elements at the open ends can be configured to close the open ends. In some embodiments, the first closing element can secure the first open end to a medical dressing. In some embodiments, the tubing can include a central line, an IV line, a peripherally inserted central catheter (PICC) line and/or a hemodialysis line. In some embodiments, the encasement device can include a movable flap coupled to the flexible sleeve. The flap can open to allow access to the tubing and any other components connected to the tubing and the flap can close to protect the tubing and such components from contaminants.

In some aspects, a device includes a flexible sleeve sized to receive and enclose a set of one or more medical lines connected to a patient, the flexible sleeve having first and second ends and a flexible body extending between the first and second ends. The flexible sleeve includes one or more antimicrobial agents disposed throughout an entire length of the flexible body. The device includes a first closing element disposed at the first end of the flexible sleeve. The first closing element selectively opens and closes the first end of the flexible sleeve. The second closing element is disposed at the second end of the flexible sleeve. The second closing element selectively opens and closes the second end of the flexible sleeve. The first and second closing elements open the first and second ends of the flexible sleeve such that the flexible sleeve can be placed around the set of medical lines. The first and second closing elements close the first and second ends of the flexible sleeve around the set of medical lines at the first and second ends of the flexible sleeve such that the flexible sleeve is configured to protect the set of medical lines from contaminants.

In some aspects, a device includes a flexible sleeve sized to receive and enclose a set of one or more medical lines connected to a patient. The flexible sleeve has first and second ends and a flexible body extending between the first and second ends. The device includes a first closing element disposed at the first end of the flexible sleeve. The first closing element selectively opens and closes the first end of the flexible sleeve. The device includes a second closing element disposed at the second end of the flexible sleeve. The second element selectively opens and closes the second end of the flexible sleeve. The first and second closing elements open the first and second ends of the flexible sleeve such that the flexible sleeve can be placed around the set of medical lines. The first and second closing elements close the first and second ends of the flexible sleeve around the set of medical lines at the first and second ends of the flexible sleeve such that the flexible sleeve is configured to protect the set of medical lines from contaminants. The device further includes a perforation line formed in the flexible sleeve and extending along a longitudinal length of the flexible sleeve. The perforation line allows the flexible sleeve to be opened along the longitudinal length of the flexible sleeve such that the flexible sleeve can be removed from the set of medical lines.

In some aspects, a device includes a flexible sleeve sized to receive and enclose a set of medical lines connected to a patient. The flexible sleeve has first and second ends and a flexible body extending between the first and second ends. The set of medical lines includes a catheter terminating in one or more connectors and one or more lines configured to couple to the one or more connectors. The device includes at least one closing element, the at least one closing element disposed at the first or second end of the flexible sleeve and configured to selectively open and close the first or second end. The at least one closing element opens the first or second end of the flexible sleeve such that the flexible sleeve can be placed around the set of medical lines. The at least one closing element closes the first or second end of the flexible sleeve around the set of medical lines at the first or second end of the flexible sleeve such that the flexible sleeve is configured to protect the set of medical lines from contaminants. The device includes a lateral opening closing element configured to reversibly close a lateral opening formed in the flexible body at a location near the one or more connectors. The lateral opening closing element opens to allow access to the one or more connectors. The lateral opening closing element closes to protect the set of medical lines from contaminants.

In some aspects, a device includes a flexible sleeve sized to receive and enclose a set of one or more medical lines connected to a patient. The set of medical lines includes a medical line disposed through an insertion site. The flexible sleeve has first and second ends and a flexible body extending between the first and second ends, the first end of the flexible sleeve defining an opening and the second end of the flexible sleeve with a closing element or being permanently closed. The device includes a flange disposed at the first end of the flexible sleeve, the flange surrounding the opening and having an adhesive surface. The adhesive surface directly attaches to a dressing or surface at the insertion site such that the flange encircles the catheter and the flexible sleeve closes around the set of medical lines. The adhesive surface detaches from the dressing or surface in response to a peeling force applied by a user to the flange.

BRIEF DESCRIPTION OF THE DRAWINGS

FIG. 2 is an illustration of an encasement for protection of one or more lines from contaminants, according to an embodiment.

FIG. 4 is an illustration of an encasement for protection of one or more lines from contaminants, according to an embodiment.

FIG. 5 is an illustration of an encasement with a flap for protection of one or more lines from contaminants, according to an embodiment.

FIGS. 6A and 6B are illustrations of a collection of packs for packaging of encasements, according to an embodiment.

FIGS. 8A-8G are illustrations of a method of protecting a line from contaminants, according to various embodiments.

FIG. 9 is a block diagram of a method of protecting a line from contaminants, according to an embodiment.

FIGS. 12A-C are illustrations of encasements for protection of one or more lines from contaminants, according to various embodiments.

DETAILED DESCRIPTION

Figure 1:
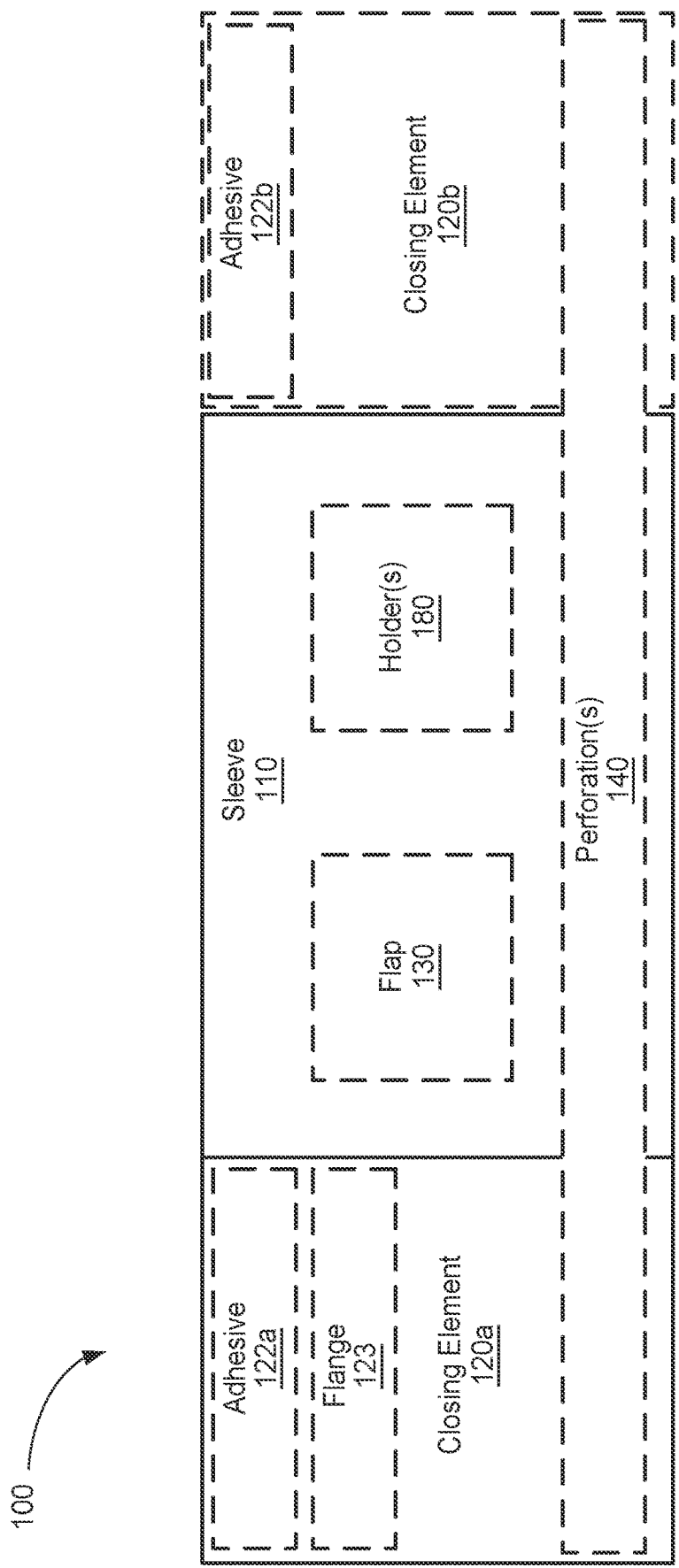
FIG. 1 is a block diagram of an encasement for protection of one or more lines, ports, and/or connection sites (e.g., IV tubing) from contaminants, according to an embodiment.

Bloodstream infections in patients with central lines are a costly and preventable danger to patient health and safety. A central line is a tube placed into a large vein of a patient in order to administer medical treatment and can potentially be a major point of contamination or infection. HAI's cause significant loss of life and financial burden in the healthcare community. Some of the most dangerous HAI's are CLABSI's and catheter-related bloodstream infections (CRBSI). According to the CDC, up to one in four people who contract CLABSI's or CRBSI's die. Estimates show the average cost to treat CLABSI is more than $45,000 per infection. Preventing CLABSI's can include a focus on protecting the central line both during its insertion and its maintenance, both of which present opportunities for the introduction of microorganisms.

Many variables can contribute to bloodstream infections, including intrinsic risk factors related to the patient's age or underlying diseases, and extrinsic risk factors such as lack of maximal sterile barriers during insertion and multiple central venous catheters. Patients often only have one central line inserted at a time, but the handling of the central line after insertion can lead to infection problems. CLABSI reduction initiatives are often successful when they eliminate as many variables as possible. This can be a three-prong approach, that includes the people in contact with the patient, the standards of the healthcare facility, and the technology employed in the implementation of the central line. These three factors can each be important and are often seen as interdependent.

Effective products can aid medical professionals in reducing infections. Products that are easy to use and designed to help medical professionals comply with industry best practices and standards are important for crucial patient care tasks. Such tasks can include securing catheters and protecting IV lines from contamination. In some cases, a blend of products working in concert, alongside evolving procedures and standards provide a scenario to reduce infection rates.

Conventional medical barriers and dressings can be used in many contexts, including wound dressings, post-surgical dressings, and other specialized situations. Catheters allow the drainage of fluids, injection of fluids, or access by surgical instruments (e.g., arterial lines for angioplasty). Problems occur with prolonged use of a catheter/IV or drainage tube, as the prolonged use allows for biofilm formation and/or creates a site for contamination both at the surface and at access ports of the IV, which are often exposed to touch and airborne contaminations. Conventional barriers often protect a wound or catheter/IV site against microbes and infections. In some instances, the barrier can cover the catheter entry point, but surrounding areas (such as IV access points and proximal areas during IV use) are susceptible to contamination, such as IV access points and proximal areas during IV use. Catheter/IV manipulation, patient transport, and environmental factors including bodily fluids, surface contact and IV manipulation in between routine cleaning procedures often allow vectors for contamination and infection that are difficult to practically mitigate with intermittent cleaning procedures. Cleaning procedures often only include daily chlorhexidine skin cleaning alongside constant re-positioning of IV lines in an attempt to keep them clear of contaminated areas. There are no widely adopted protocols for cleaning IV lines. Ports are usually cleaned with alcohol or povidone-iodine (e.g., Betadine®) before and after use.

Short-term catheters and long-term catheters can be non-tunneled or tunneled. A short-term, non-tunneled catheter can stay in place for days or weeks. A long-term tunneled catheter can stay in place for months or years. Examples of both short-term and long-term catheters include Central Venous Catheters (CVC), PICC lines, hemodialysis catheters, apheresis catheters, and arterial line catheters. Catheters are inserted under the skin into a large vein or artery. The catheter lumens or ports exits outside of the body and allows for vascular access for administration of fluid, blood, medication, and/or nutrition, and/or for removal of fluid and/or blood. Arterial lines are catheters inserted into an artery either on the wrist of an arm or in the groin area to either monitor the blood pressure, for blood draw, or to infuse a medication to break down a blood clot that occludes an artery.

Each entry into the access points in the delivery systems is an opportunity to introduce microorganisms. The post-CVC insertion period presents multiple opportunities for the risk of infection. The proper maintenance of lines is important for continued patient safety. Recent reports to the National Healthcare Safety Network (NHSN) by Pennsylvania's acute care hospitals assert that nearly 72% of al CLABSI's occurred more than 5 days after insertion. This suggests that infection prevention lapses oftentimes occur in the post insertion care and maintenance of the CVC's.

When not in use, catheter ports are cleaned and covered with a disinfecting cap, and the line is clamped. However, IV lines and IV connection sites are left exposed to microbes on skin and the surrounding environment. The hubs on central venous catheters (CVC) are a common source of bacterial colonization and serve as an immediate portal of entry for microorganisms to the intraluminal surface of the catheter. These colonizers from the catheter hub and lumen can be dispersed into the bloodstream resulting in CLABSI. In long term CVC's, the needleless connectors (NC) and catheter hubs are more frequently accessed and can potentially lead to CLABSI's. The disinfection of a catheter hub surface every time before it is accessed is therefore important.

Exposed IV lines are widely recognized as a point for contamination from routine handling, bodily fluids, vomit, and excrement, which can each harbor a variety of microorganisms that may cause infection, if handling the port area. While aseptic technique per CDC required CLABSI bundle is followed, in practicality, patients may have a line in a complex position, complex line routing (e.g., around a groin, armpit, etc.), and/or an area of repeated exposure to contaminants. The biofilm contamination may lead to CLABSI when microbes migrate to ports or when microbes are transferred onto the ports when contaminated IV lines are handled and the port is accessed.

Preparation(s) or cleaning(s) of the insertion site, the dressing and the IV lines often includes cleansing with alcohol, chlorhexidine, or similar chemicals. This can be a preparation routine for surgery or for daily routines. There is currently no protocol for cleaning the lines themselves. Presently, IV lines and IV connection sites are protected by wiping the skin once a day with chlorhexidine and by moving lines away from obvious sources of contamination. Access ports can be cleaned with alcohol, and disinfecting caps (e.g., Curos™ caps) can be included in a delivery system. Cleaning can be done when injecting multiple different medications though the port, and another disinfecting cap is added at the end of the cleaning. Skin cleaning is often only required or done once per day, allowing buildup of potential biofilm. This can lead to several problems. First, the area can become susceptible to recontamination via touching and/or airborne organisms or contaminants. Second, this can contribute to organisms' resistance to cleaners and antimicrobials. Additional issues can occur when adding antimicrobial agents that may be insufficient and ineffective, or antimicrobial agents that are over-aggressive, causing harm or damage to tissue. Most antimicrobial products are incorporated into dressings or seals primarily focusing on the skin-to-IV insertion site contact point. Presently, there are no IV covering solutions for IV's in use.

Existing solutions do not incorporate continuous antimicrobial protection of the exposed IV line. Disinfecting caps and advanced dressings can aim to solve some issues but fail to address problems concerning clean lines and provide facile access to lines. Embodiments described herein can work with or without adjacent solutions to increase infection prevention.

Prolonged and continuous protection of IV lines while retaining intuitive functional access can be desirable. Preventing CLABSI in an efficacious and cost-effective manner without compromising physical access of IV lines in use is also important.

Embodiments described herein generally relate to IV and/or catheter encasements or coverings, systems and components thereof, and methods of making the same. In some embodiments, encasements described herein can include sleeves (e.g., coverings with open ends or multiple openings) or bags (e.g., coverings or containers with an opening at one end). In some embodiments, encasements described herein can include sleeves with open ends permitting IV-line entry and exit and closing elements (e.g., cinch elements) at both ends to facilitate selective closure and opening, (e.g., to permit line access). Closing elements can allow for access to the IV and/or catheter, removal of the encasement, and/or re-closing. In some embodiments, adhesive flanges can be included on none, one, or both ends of a sleeve. In some embodiments, a sleeve can include an adhesive flange at a first open end and a closure element at a second open end. The encasements described herein can be used to protect critical points and areas of the IV line that are prone to contamination. These can include entry points, port access points, dressing entry points, and/or other critical points and areas of the IV line.

In some embodiments, an encasement can be composed of a polymer or other suitable flexible material. In some embodiments, the encasement can be composed of a thermoplastic material capable of forming an effective barrier to contamination and being subjected to repeated manipulation and/or adjustments during the lifetime of the use of the sleeve. In some embodiments, the thermoplastic material can be embedded with, layered, and/or coated with one or more antimicrobial materials or moieties. In some embodiments, the antimicrobial materials can include bioactive materials, bioactive metals, silver, copper, zinc, nickel, cobalt, molybdenum, an oligodynamic metal, an organic antimicrobial, an organic moiety formed of one or more essential oils, an ionic polymer, an ionic oligomer, an ionic rubber, an organometallic material, effective antimicrobial organic compounds, or any other suitable antimicrobial materials or combinations thereof.

In some embodiments, the encasement can extend beyond critical points of access and contamination for additional protection and coverage of IV lines, ports, and/or sites of manipulation. In some embodiments, the encasement can include holders for mounting and/or securement of the IV lines in a desired position and/or configuration relative to the encasement. In some embodiments, the encasement can include adhesive strips on the encasement for securing on a desired surface. In some embodiments, a flap (e.g., an access point, window, and/or door) can be included on the sleeve. The flap can permit repeated access to IV lines, ports, and/or key areas between the terminal ends of the encasement without necessitating removal of the encasement. In some embodiments, the flap can be resealable, permitting reclosure of the encasement barrier and protection of IV lines during or after IV access or activity.

Methods described herein can address several drawbacks of existing solutions for reducing IV line infections. These can include, for example, coverage of IV in use, while allowing central lines to remain active and/or readily accessible. These can also include, for example, ease of access to IV points that are often critical areas of contamination if uncovered. Durability for continued use while IV lines are active, in use, or in between medical treatment can be an additional improvement. Antimicrobial activity towards continuous exposure in areas of high contamination risk (e.g., saliva, feces, vomitus, phlegm, food, skin, gown, linen, surface and floor contact, etc.) can be reduced using the methods described herein. For example, the closure of the ends of a sleeve with drawstrings, adhesives, and/or seals can permit repeated facile access to IV lines without requiring removal of the IV enclosure. In some embodiments, an adjustable adhesive flange can work in concert with dressings to form an effective contiguous barrier to infection.

Encasements described herein can be configured to provide antimicrobial or infection reduction properties during prolonged use while maintaining ease of IV line access during treatment. As a result of these advantageous properties, the encasements prepared according to the disclosed methods can be used with a variety of medically useful articles. In some embodiments, the disclosed encasements can be used to provide durable and more effective barriers to CLABSI, either alone or in combination with existing dressings. Additionally, the disclosed encasements can provide more effective access to lines when in use when compared to standard IV coverings, wraps, or dressings.

CDC guidelines for reducing infections focus on practices for inserting central lines, maintaining and handling lines, and removal of unnecessary lines. Devices described herein are configured to encase central line access ports and/or tubing in an antimicrobial environment to prevent prolonged exposure to pathogens found on a patient's skin and in surrounding environment. In some embodiments, a sterile sleeve can be configured to slide over central line connection sites, access ports, and IV tubing and to encase or cover such components to decrease biological burden on these potential pathogen entry points. In some embodiments, the outside of the sleeve can be antimicrobial and/or act as a physical barrier to prevent access ports and IV tubing from coming into direct contact with potential pathogens on the patient's skin and in the environment. In some embodiments, the sleeve can cover the central line connection sites closest to the patient, run the length of the central line, and extend to where the tubing connects to the IV pump. In some embodiments, both ends of the sleeve can be drawn closed, adhesively sealed, and/or cinched closed to keep them in place. In some embodiments, the sleeve can be formed of a flexible material such as, for example, a polymer.

Embodiments described herein can also be used on peripheral lines, which may not impose as high a risk for infection but can nevertheless have benefits from inclusion of an encasement. While several of the embodiments described herein are described in reference to hospital settings, it can be appreciated that such embodiments can be used for patients outside of the hospital, such as those receiving infusions (e.g., on a daily basis) at home. In such applications, the lines can be constantly covered or covered for a prolonged period of time. Where disposal of the encasement device is necessary, e.g., in environments outside of a hospital, embodiments described herein may utilize a biodegradable variant to minimize ecological impact.

Encasement devices such as pouches, bags, and/or sleeves described herein can also be suitable for children or pediatric patients with lines, e.g., in a hospital or at home. Children can be more active, and therefore risk of infection associated with children can be higher. Use of antimicrobial infused IV lines and catheters can be less effective in pediatric patients, whereas the physical barrier formed by the encasements described herein can provide higher efficacy in preventing problematic infections related to IV lines. Moreover, the encasement devices described herein can be used to bundle together lines and/or to secure lines to a patient's bed or other nearby structure, further reducing movement of such lines and potential infection. In some embodiments, the ability to bundle and secure lines can also improve risk of accidental line removal from pediatric patients and/or undesirable entanglement of lines with the patients and/or nearby structure.

In some embodiments, encasement devices described herein can be configured to fold into a compact configuration for storage and/or disposal. For example, an encasement device can be implemented as a sterile, folded up sleeve made of thin, sturdy, anti-microbial plastic. In some embodiments, the sleeve can protect central lines from immediately above the patient's IV ports to the IV pump.

FIG. 1 is a block diagram of a device 100 for protection of one or more central lines from contaminants, according to an embodiment. As shown, the device 100 includes an encasement or sleeve 110 and at least one closing element 120a, 120b (collectively referred to as closing elements 120). In some embodiments, the device 100 can include adhesives 122a, 122b (collectively referred to as adhesives 122) disposed on and/or incorporated into the closing elements 120. In some embodiments, the device 100 can optionally include a flange 123 incorporated into one of the closing elements 120 (e.g., closing element 120a that is situated near a catheter site). In some embodiments, the device 100 can include a flap 130, perforation(s) 140, and/or a holder 180.

In some embodiments, the sleeve 110 can be composed of one or more thermoplastics, including but not limited to: polyvinyl chloride (PVC), polypropylene (PP), polyethylene (PE)—including low-density, linear low-density, medium-density, high-density polyethylene (LDPE, LLDPE, MDPE, HDPE), polystyrene (PS), Nylon, polyethylene terephthalate (PET, PETG), polyimide (PA), polycarbonate (PC), polytetrafluorethylene (PTFE), acrylonitrile butadiene (ABS), polyetheretherketone (PEEK), polyurethane (PU), rubbers, polydimethylsiloxane (PDMS), thermoplastic polyurethanes (TPU), or any other suitable material or combinations thereof.

In some embodiments, the sleeve 110 can be composed of environmentally friendly materials (e.g., compostable and/or biodegradable) materials. Accordingly, in some embodiments, the sleeve 110 can be composed of a bioplastic. In some embodiments, the sleeve 110 can be composed of a naturally, or synthetically, derived biopolymer including but not limited to polylactic acid (PLA), polyhydroxyalkanoates (PHA), Polyhydroxybutyrate (PHB), poly-(3-hydroxybutyrate-co-3-hydroxyhexanoate (PHBH), poly-(3-hydroxybutyrate-co-3-hydroxyvalerate (PHBV), polyvinyl alcohol (PVOH), polybutylene succinate (PBS), rubbers, copolymers, or any other suitable biopolymer or combinations thereof. In some embodiments, the sleeve 110 can be composed of a naturally occurring material, such as starch, cellulose, nanocellulose, lignin, hemicellulose, chitin, chitosan, beta-glucans, glucan, or any other suitable material, or combinations thereof.

In some embodiments, the sleeve 110 can be composed of a blend or mix of one or more of the aforementioned polymers, biopolymers, and/or additives. In some embodiments, the sleeve 110 can be composed of a material to support biodegradation, composting, hydrolysis, and/or rapid degradation in the environment.

In some embodiments, the sleeve 110 can be modified using fillers and/or additives for tuning aesthetic, function, texture, surface smoothness, density, strength, heat-resistance, or other physical characteristics. Such additives may include, but are not limited to: pigments, clarifiers, talc, minerals, calcium carbonates, diatomaceous earths, fire-retardants, fibers, copolymers, stabilizers, lubricants, plasticizers, foaming agents, anti-inflammatory agents, antimicrobials, antifungals, or any combination thereof.

In some embodiments, the sleeve 110 can include antimicrobial additives or antimicrobial agents, e.g., to support efficacy of infection prevention during prolonged use. Such additives can include one or more antimicrobial categories, such as oligodynamic metals (e.g., silver, zinc, copper, nickel, and/or derived alloys including but not limited to brasses, bronzes, cupronickel, copper-nickel-zinc, and/or ionized derivatives), antimicrobial organics including but not limited to organic moieties found in essential oils, ionic polymers and oligomers, ionic rubbers, organometallics, and/or other antimicrobial compounds. In some embodiments, antimicrobial additives can be embedded and distributed within the sleeve 110. In some embodiments, the antimicrobial additives can be coated onto one or many or all external and/or internal surfaces of the sleeve 110. In some embodiments, the antimicrobial additives can coat an inner surface of the sleeve 110. In some embodiments, the antimicrobial additives can coat an outer surface of the sleeve 110. In some embodiments, a first antimicrobial additive can be embedded in the sleeve 110 while a second antimicrobial additive can coat the inner surface and/or the outer surface of the sleeve 110. In some embodiments, one or more antimicrobial additives can be disposed throughout an entire length of the sleeve 110. In some embodiments, the second antimicrobial additive can be different from the first antimicrobial additive. In some embodiments, the second antimicrobial additive can have a different chemical composition from the first antimicrobial additive.

In some embodiments, the sleeve 110 can be opaque. In some embodiments, the sleeve 110 can be at least partially transparent. In some embodiments, the sleeve 110 can have an optical transmittance of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85%. In some embodiments, the sleeve 110 can have an optical transmittance of no more than about 90%, no more than about 85%, no more than about 80%, no more than about 75%, no more than about 70%, no more than about 65%, no more than about 60%, no more than about 55%, no more than about 50%, no more than about 45%, no more than about 40%, no more than about 35%, no more than about 30%, no more than about 25%, no more than about 20%, or no more than about 15%.

Combinations of the above-referenced optical transmittance values are also possible (e.g., at least about 10% and no more than about 90% or at least about 50% and no more than about 70%), inclusive of all values and ranges therebetween. In some embodiments, the sleeve 110 can have an optical transmittance of about 10%, about 15%, about 20%, about 25%, about 30%, about 35%, about 40%, about 45%, about 50%, about 55%, about 60%, about 65%, about 70%, about 75%, about 80%, about 85%, or about 90%.

In some embodiments, the sleeve 110 can include an opaque or substantially opaque label patch disposed thereon. In some embodiments, the opaque label patch can include writing thereon.

In some embodiments, the sleeve 110 can be waterproof, e.g., to protect lines and/or tubing encased or covered by the sleeve 110 from contamination. In some embodiments, the sleeve 110 can be tinted in different colors. In some embodiments, the sleeve 110 can be available in different colors to make the sleeve 110 and the enclosed lines more visible to healthcare staff, thereby reducing the tripping hazard associated with the central lines. In some embodiments, different color sleeves can be used to identify different types of lines, e.g., central or peripheral, and/or uses for different patient populations, e.g., higher or lower risk patient. In some embodiments, the sleeve 110 can be at least partially transparent or translucent, e.g., to make the enclosed lines visible to healthcare staff, thereby facilitating manipulation and/or identification of particular lines.

The sleeve 110 can be sized to receive and enclose a set of one or more medical lines connected to a patient. In some embodiments, the sleeve 110 can enclose at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, or at least about 19 medical lines. In some embodiments, the sleeve 110 can enclose no more than about 20, no more than about 19, no more than about 18, no more than about 17, no more than about 16, no more than about 15, no more than about 14, no more than about 13, no more than about 12, no more than about 11, no more than about 10, no more than about 9, no more than about 8, no more than about 7, no more than about 6, no more than about 5, no more than about 4, no more than about 3, or no more than about 2 medical lines. Combinations of the above-referenced number of medical lines enclosed by the sleeve 110 are also possible (e.g., at least about 1 and no more than about 20 or at least about 2 and no more than about 5), inclusive of all values and ranges therebetween. In some embodiments, the sleeve 110 can enclose about 1, about 2, about 3, about 4, about 5, about 6, about 7, about 8, about 9, about 10, about 11, about 12, about 13, about 14, about 15, about 16, about 17, about 18, about 19, or about 20 medical lines.

The sleeve 110 can be formed from any suitable process for forming a flexible component that is sized to fit around one or more lines or tubing (e.g., central lines or IV lines). In some embodiments, the sleeve 110 can be formed from an extrusion process, such as, for example, a blown film extrusion process. In some embodiments, the sleeve 110 can have a thickness of at least about 100 μm, at least about 200 μm, at least about 300 μm, at least about 400 μm, at least about 500 μm, at least about 600 μm, at least about 700 μm, at least about 800 μm, at least about 900 μm, at least about 1 mm, at least about 1.1 mm, at least about 1.2 mm, at least about 1.3 mm, at least about 1.4 mm, at least about 1.5 mm, at least about 1.6 mm, at least about 1.7 mm, at least about 1.8 mm, or at least about 1.9 mm. In some embodiments, the sleeve 110 can have a thickness of no more than about 2 mm, no more than about 1.9 mm, no more than about 1.8 mm, no more than about 1.7 mm, no more than about 1.6 mm, no more than about 1.5 mm, no more than about 1.4 mm, no more than about 1.3 mm, no more than about 1.2 mm, no more than about 1.1 mm, no more than about 1 mm, no more than about 900 µm, no more than about 800 µm, no more than about 700 µm, no more than about 600 µm, no more than about 500 µm, no more than about 400 µm, no more than about 300 µm, or no more than about 200 µm. Combinations of the above-referenced thickness ranges are also possible (e.g., at least about 100 µm and no more than about 2 mm or at least about 300 µm and no more than about 1 mm), inclusive of all values and ranges therebetween. In some embodiments, the sleeve 110 can have a thickness of about 100 µm, about 200 µm, about 300 µm, about 400 µm, about 500 µm, about 600 µm, about 700 µm, about 800 µm, about 900 µm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm. In some embodiments, the sleeve 110 can be thin enough, such that it can fit through closed doors.

The sleeve 110 can have a length that is suitable for extending a full length of one or more lines or tubing, e.g., from a catheter site (e.g., a dressing site) to a IV bag, pump, or other external component coupled to a catheter line. In some embodiments, the sleeve 110 can have a length of at least about 1 cm, at least about 2 cm, at least about 3 cm, at least about 4 cm, at least about 5 cm, at least about 6 cm, at least about 7 cm, at least about 8 cm, at least about 9 cm, at least about 10 cm, at least about 20 cm, at least about 30 cm, at least about 40 cm, at least about 50 cm, at least about 60 cm, at least about 70 cm, at least about 80 cm, at least about 90 cm, at least about 1 m, at least about 2 m, at least about 3 m, at least about 4 m, at least about 5 m, at least about 6 m, at least about 7 m, at least about 8 m, or at least about 9 m. In some embodiments, the sleeve 110 can have a length of no more than about 10 m, no more than about 9 m, no more than about 8 m, no more than about 7 m, no more than about 6 m, no more than about 5 m, no more than about 4 m, no more than about 3 m, no more than about 2 m, no more than about 1 m, no more than about 90 cm, no more than about 80 cm, no more than about 70 cm, no more than about 60 cm, no more than about 50 cm, no more than about 40 cm, no more than about 30 cm, no more than about 20 cm, no more than about 10 cm, no more than about 9 cm, no more than about 8 cm, no more than about 7 cm, no more than about 6 cm, no more than about 5 cm, no more than about 4 cm, no more than about 3 cm, or no more than about 2 cm.

Combinations of the above-referenced lengths of the sleeve 110 are also possible (e.g., at least about 1 cm and no more than about 10 mm or at least about 5 cm and no more than about 50 cm), inclusive of all values and ranges therebetween. In some embodiments, the sleeve 110 can have a length of about 1 cm, about 2 cm, about 3 cm, about 4 cm, about 5 cm, about 6 cm, about 7 cm, about 8 cm, about 9 cm, about 10 cm, about 20 cm, about 30 cm, about 40 cm, about 50 cm, about 60 cm, about 70 cm, about 80 cm, about 90 cm, about 1 m, about 2 m, about 3 m, about 4 m, about 5 m, about 6 m, about 7 m, about 8 m, about 9 m, or about 10 m.

In some embodiments, the sleeve 110 can include one or more coupling elements (not shown) disposed along a length of the sleeve 110. The coupling element can be configured to couple or attach one or more portions of the sleeve 110 to nearby structures (e.g., a patient bed, an IV pole, walls, furniture, medical equipment, etc.), e.g., to secure lines and sleeves for safety and convenience. In an embodiment, the coupling elements can be implemented as mounting loops or straps. The mounting loops can include elastic elements (e.g., elastic string) that are attached to adhesive strips or pads each with a removable mounting sticker. The stickers can be removed to expose adhesive portions that can be used to secure or tether a portion of the sleeve to an object. Additionally, or alternatively, one or more coupling elements can include other structure for attaching to objects, e.g., hooks, fasteners, clamps, etc. While the sleeve 110 can protect lines and other tubing from potential exposure to pathogens, it can also be used to protect sensitive lines and/or lines that may be exposed to the floor or other environments where damage to the lines may be possible. Additionally or alternatively, the coupling elements can allow healthcare workers to keep the sleeve 110 and catheter lines out of certain areas, e.g., so they pose less of a hazard for tripping, which could cause injury to the healthcare professional or the patient. In some embodiments, the sleeve 110 can be discarded and replaced at the same time one or more lines are exchanged or removed.

The closing elements 120 can have one or more mechanisms to close terminal ends of the sleeve 110. The closing elements 120 can be configured to transition the terminal ends of the sleeve 110 between a closed or sealed configuration and an open configuration. In the open configuration, the terminal ends of the sleeve 110 can permit passage of one or more catheter lines. In the closed or sealed configuration, the terminal ends of the sleeve 110 can close around one or more catheter sites or lines, e.g., securing the sleeve 110 in place and enhancing the effectiveness of the barrier created by the sleeve 110. In some embodiments, closure types and mechanisms employed in the closing elements 120 can include a drawstring and/or a cinch. In some embodiments, the drawstring and/or cinch can include a cord. In some embodiments, the drawstring and/or cinch can be braided. In some embodiments, the drawstring and/or cinch can be composed of plastic, rubber, polymer, or any other suitable material or combinations thereof. In some embodiments, the drawstring and/or cinch can include stopper snaps disposed thereon. In some embodiments, the stopper snaps can include round buttons (e.g., snap fit buttons) disposed on an elastic drawstring that can couple to one another to tighten the sleeve 110 around the catheter lines and keep the sleeve 110 in place. In some embodiments, the stopper snaps can be made of a rubbery material and can slide along the length of an elastic cord to tighten the sleeve 110 and secure the sleeve 110 in place. In some embodiments, one or more elastic cords of the closing elements 120 can be disposed in a channel, fold, or seam at either end of the sleeve 110. In some embodiments, the elastic cords can include a knotted end that can be used to secure the sleeve 110 to nearby surfaces. In some embodiments, the channel in which the closing elements 120 are disposed can be made by folding over the material of the sleeve 110 and securing it in place (e.g., via an adhesive and/or stitching). After forming the channel, the elastic cords can be extended through the channel and knotted. In use, a healthcare worker can slide the stopper snaps along the elastic cord to tighten the sleeve around the central lines and snap them closed to keep the sleeve 110 secured around the lines. In some embodiments, a portion of the knotted end of the elastic cord can be used to affix or secure the sleeve 110 to an appropriate surface or object.

In some embodiments, the closing elements 120 can optionally include adhesives 122. In some embodiments, the adhesives 122 can include self-adhesives, two-sided adhesives, one-sided adhesives, flap-hinged adhesives, resealable adhesives, or any other suitable adhesives or combinations thereof. In some embodiments, at least one of the closing elements 120 (e.g., closing element 120a) can include a flange 123. In some embodiments, the flange can be an adhesive flange, which can be a peel strength adhesive flange, an angle adhesive flange, or any other suitable adhesive flange or combinations thereof. The flanges 123 can provide a surface for adhering to a medical dressing. The flanges 123 can adhere to a medical dressing overlaying an insertion site. In some embodiments, the flanges 123 can encircle the insertion site. In some embodiments, the adhesive 122a and/or the adhesive 122b can adhere to itself and/or an inner or outer surface of the sleeve 110 to close around the central line. In some embodiments, the closing element 120a and/or the closing element 120b can be configured to selectively open and close the terminal ends of the sleeve 110. In some embodiments, the adhesive 122a and/or the adhesive 122b can adhere to close around the central line without adhering to a dressing. In some embodiments, the adhesives 122 can include an adhesive pad or strip that can selectively open and close multiple times. In some embodiments, the flange 123 can have a rectangular shape, a square shape, a round shape, an annular shape, a trigonal shape, a hexagonal shape, an octagonal shape, or any other suitable shape.

In some embodiments, the adhesive flange can have a peel strength of at least about 1 N/25 mm, at least about 2 N/25 mm, at least about 3 N/25 mm, at least about 4 N/25 mm, at least about 5 N/25 mm, at least about 6 N/25 mm, at least about 7 N/25 mm, at least about 8 N/25 mm, at least about 9 N/25 mm, at least about 10 N/25 mm, at least about 12 N/25 mm, at least about 14 N/25 mm, at least about 15 N/25 mm, at least about 16 N/25 mm, at least about 18 N/25 mm, at least about 20 N/25 mm, at least about 25 N/25 mm, at least about 30 N/25 mm, at least about 35 N/25 mm, at least about 40 N/25 mm, or at least about 45 N/25 mm. In some embodiments, the adhesive flange can have a peel strength of no more than about 50 N/25 mm, no more than about 45 N/25 mm, no more than about 40 N/25 mm, no more than about 35 N/25 mm, no more than about 30 N/25 mm, no more than about 25 N/25 mm, no more than about 20 N/25 mm, no more than about 18 N/25 mm, no more than about 16 N/25 mm, no more than about 15 N/25 mm, no more than about 14 N/25 mm, no more than about 12 N/25 mm, no more than about 10 N/25 mm, no more than about 9 N/25 mm, no more than about 8 N/25 mm, no more than about 7 N/25 mm, no more than about 6 N/25 mm, no more than about 5 N/25 mm, no more than about 4 N/25 mm, no more than about 3 N/25 mm, or no more than about 2 N/25 mm. Combinations of the above-referenced peel strengths are also possible (e.g., at least about 1 N/25 mm and no more than about 50 N/25 mm or at least about 5 N/25 mm and no more than about 25 N/25 mm), inclusive of all values and ranges therebetween. In some embodiments, the adhesive flange can have a peel strength of about 1 N/25 mm, about 2 N/25 mm, about 3 N/25 mm, about 4 N/25 mm, about 5 N/25 mm, about 6 N/25 mm, about 7 N/25 mm, about 8 N/25 mm, about 9 N/25 mm, about 10 N/25 mm, about 12 N/25 mm, about 14 N/25 mm, about 15 N/25 mm, about 16 N/25 mm, about 18 N/25 mm, about 20 N/25 mm, about 25 N/25 mm, about 30 N/25 mm, about 35 N/25 mm, about 40 N/25 mm, about 45 N/25 mm, or about 50 N/25 mm.

In some embodiments, the closing elements 120 can include hook and loop closing elements, self-fasteners, self-closures, zip top closures, snap-button closures, press-to-seal closures, snap closures, Velcro closures, or any other suitable closures or combinations thereof. In some embodiments, the closing element 120a can include a first closing mechanism and the closing element 120b can include a second closing mechanism, the second closing mechanism different from the first closing mechanism. For example, the closing element 120a can include an adhesive flange, while the closing element 120b can include a drawstring closure.

While sleeve 110 is depicted with two closing elements 120a, 120b, e.g., disposed at the opposite ends of the sleeve 110, it can be appreciated that any number of closing elements 120a, 120b can be part of device 100. For example, in some embodiments, a sleeve 110 can have one end that can open and close and an opposite end that is permanently closed (e.g., sealed). In such embodiments, the sleeve 110 may only have a single closing element 120a. In other words, the sleeve 110 can effectively act as a bag with one open end and one closed end. In other embodiments, the sleeve 110 can have multiple closing elements 120 disposed along a length of the sleeve 110, e.g., to secure the sleeve 110 around internal lines at multiple points and/or to secure the sleeve 110 to nearby surfaces or objects at multiple points. In some embodiments, the closing elements 120 can include stopper snaps to secure the closing elements 120 in place.

In some embodiments, an adhesive flange incorporated into one or more of the closing elements 120 can be configured to attach to various surfaces (e.g., medical dressings, patient skin, etc.). In some embodiments, an adhesive flange that is attached to a particular surface can be designed to be removed at a low peel strength, e.g., to prevent disruption of an existing dressing. In some embodiments, the sleeve 110 can be discarded after a single removal. In some embodiments, the adhesive flange can have adhesive properties and peel strength for repeated manipulation, adjustment, or placement, such that the encasement may be accessed repeatedly throughout use, not disrupt the foundation dressing, and retain effective adhesion strength through multiple uses. In such embodiments, the adhesive flange can be replaced on the dressing one or more times, e.g., forming effective barrier properties for continued use until discarded. In some embodiments, the adhesive forming the seal of the adhesive flange can be embedded and/or coated with antimicrobial additives.

In some embodiments, the sleeve 110 can include a higher concentration of antimicrobial additives at the terminal ends of the sleeve 110 than near the center of the sleeve 110.

In some embodiments, a cinch style closure method such as a drawstring or cord may be used at the end of the sleeve 110 to close the sleeve 110 firmly around one or more catheter lines. In some embodiments, the drawstring/cord of the cinching mechanism incorporated into the closing elements 120 can be composed of a synthetic material, e.g., to prevent liquid absorption. In some embodiments, the drawstring/cord of the cinching mechanism incorporated into the closing elements 120 can include antimicrobial materials. In some embodiments, the drawstring/cord of the cinching mechanism incorporated into the closing elements 120 can include end-tabs for dexterity and/or fray prevention. In some embodiments, seams or folds can be formed, e.g., to envelop one or more components of the closing elements 120 (e.g., the cords/cinch tool, cord, etc.), using techniques such as flange roll (e.g., sleeve 110 being wrapped around a cinching mechanism or portion thereof) and then sealed using heat, impulse sealing, sonic sealing, or other suitable techniques.

In some embodiments, the sleeve 110 can optionally include a flap 130 that can allow for access to the catheter lines within the sleeve 110 without removal of the sleeve 110 and/or largescale manipulation of the sleeve 110 (e.g., scrunching of the sleeve to expose a particular part of a catheter line). The flap 130 can be positioned at a location along the sleeve 110 that access may be more often desired, e.g., a location with connector(s) and/or port(s) for connecting to other lines, ports, catheters, etc. In some embodiments, the flap 130 can include a section that is integrally formed or coupled to the sleeve 110 with a resealable surface (e.g., an adhesive surface), such that the flap 130 can be opened and closed to maintain the protective qualities of the sleeve 110 after accessing the central lines. In some embodiments, the flap 130 can include a tab attached thereto to ease pulling of the flap 130. In some embodiments, the flap 130 can have the same or substantially similar material properties to the rest of the sleeve 110. In some embodiments, the flap can have different material properties from the rest of the sleeve 110. While a single flap 130 is depicted in FIG. 1, it can be appreciated that devices described herein can include multiple flaps disposed at different locations along a longitudinal length of the sleeve 110. In some embodiments, the flap 130 can include a higher concentration of antimicrobial additives than the remainder of the sleeve 110. In some embodiments, the flap 130 can include a first portion that is attached to or integrally formed with the rest of the sleeve 110 and a second portion having one or more resealable surfaces that can couple to an exterior surface of the rest of the sleeve 110. In other words, a resealable surface on the outside of the flap 130 can reversibly couple to the outer surface of the sleeve 110 when the flap 130 is opened, in order to keep the flap 130 opened securely.

In some embodiments, the sleeve 110 can optionally include the perforation 140. The perforation 140 can allow for easy and/or immediate removal of the sleeve 110. The perforation 140 can allow the sleeve 110 to be opened along the longitudinal length of the sleeve 110 such that the sleeve 110 can be removed from the set of medical lines. In some embodiments, the perforation 140 can extend along the length of the sleeve 110. In some embodiments, the perforation 140 can extend approximately from the closing element 120a to the closing element 120b. In some embodiments, the sleeve 110 can include multiple lines of perforations 140, e.g., a first line that extends along a longitudinal length of the sleeve 110 and one or more other lines that extend around a perimeter of the sleeve 110 (e.g., circumferentially around the sleeve 110). In some embodiments, the perforation 140 can include multiple perforation lines along the length of the sleeve 110. In some embodiments, the perforation 140 can include multiple perforation lines around the perimeter of the sleeve 110. In some embodiments, one or more perforations 140 can be configured to separate portions of the sleeve 110 from one another, e.g., to separate a closing element 120 from an end of the sleeve 110.

In some embodiments, the device 100 can optionally include a holder 180. The holder 180 can be incorporated into and/or disposed within the sleeve 110, e.g., to aid in spacing and organizing the catheter lines. In some embodiments, the holder 180 can include a mechanical coupler. In some embodiments, the holder 180 can include an adhesive. In some embodiments, the holder 180 can extend between the sleeve 110 and a nearby structure or surface and couple the sleeve to the nearby structure or surface. In some embodiments, the holder 180 can include multiple notches, into which the catheter lines can be secured. In some embodiments, the holder 180 can be attached to the interior of the sleeve 110. In some embodiments, the holder 180 can be detached from the sleeve 110 such that the holder 180 is separate from the sleeve 110 and can move relative to the sleeve 110. In some embodiments, the holder 180 can be attached to the interior of the sleeve 110 (e.g., via an adhesive). In some embodiments, the holder can be attached to the exterior of the sleeve 110 (e.g., via an adhesive). In some embodiments, the holder 180 can feature a row of slots inside the sleeve 110 for placement of the catheter lines. In some embodiments, the holder 180 can be located about 1 cm, about 2 cm, about 3 cm, about 4 cm, about 5 cm, about 6 cm, about 7 cm, about 8 cm, about 9 cm, or about 10 cm from the proximal end of the sleeve 110, inclusive of all values and ranges therebetween. In some embodiments, a first end of the encasement 100 can include multiple holders 180 to properly space and organize the catheter lines.

In some embodiments, the holder 180 can be disposed near the flap 130 (e.g., less than about 10 cm, less than about 9 cm, less than about 8 cm, less than about 7 cm, less than about 6 cm, less than about 5 cm, less than about 4 cm, less than about 3 cm, less than about 2 cm, or less than about 1 cm from an outside edge of the flap 130, inclusive of all values and ranges therebetween). In some embodiments, the holder 180 can be disposed near an opening created by the lifting of the flap 130 (e.g., less than about 10 cm, less than about 9 cm, less than about 8 cm, less than about 7 cm, less than about 6 cm, less than about 5 cm, less than about 4 cm, less than about 3 cm, less than about 2 cm, or less than about 1 cm from the opening created by the lifting of the flap 130, inclusive of all values and ranges therebetween).

In some embodiments, a designated opaque area or plaque can be printed or layered on the sleeve 110, enabling clear labeling, dating, or annotating using writing utensils such as pens, markers, and/or similar items. In some embodiments, multiple devices 100 can be packaged into a package for ease of access and dispensation of the devices 100 in medical and/or home environments. In some embodiments, the device 100 can be folded in such a way to make storage and usage convenient. In some embodiments, the sleeve 110 can be folded inside itself to make it smaller, e.g., so it can be handled easily by healthcare staff.

FIG. 2 is an illustration of an encasement device 200 for protection of one or more lines or tubing (e.g., central lines) from contaminants, according to an embodiment. As shown, the encasement device 200 includes an encasement or sleeve 210, a proximal closing element 220a, and a distal closing element 220b (collectively referred to as closing elements 220). In some embodiments, the sleeve 210 and the closing elements 220 can be the same or substantially similar to the sleeve 110 and the closing elements 120, as described above with reference to FIG. 1. Thus, certain aspects of the sleeve 210 and the closing elements 220 are not described in greater detail herein.

As shown, the sleeve 210 covers access ports and other areas of central lines susceptible to infection. As shown, the proximal closing element 220a is coupled to the dressing via a strap or strip. In some embodiments, the closing element 220a can include a resealable adhesive. The resealable adhesive can be configured to selectively open and close the open end of the sleeve 210, e.g., by adhering to itself and/or an inner or outer surface of the sleeve 210. As shown, the distal closing element 220b secures over and around the lines via a drawstring apparatus. The drawstring apparatus includes a stopper that can move to tighten the distal closing element 220b. In some embodiments, the stopper can include a button that can be pushed against a spring mechanism to allow the stopper to be moved along the drawstring to tighten and loosen the drawstring. In some embodiments, the strap of the proximal closing element 220a can include an adhesive. In some embodiments, the strap of the proximal closing element 220 can seal an end of the sleeve 210.

Figure 3A:
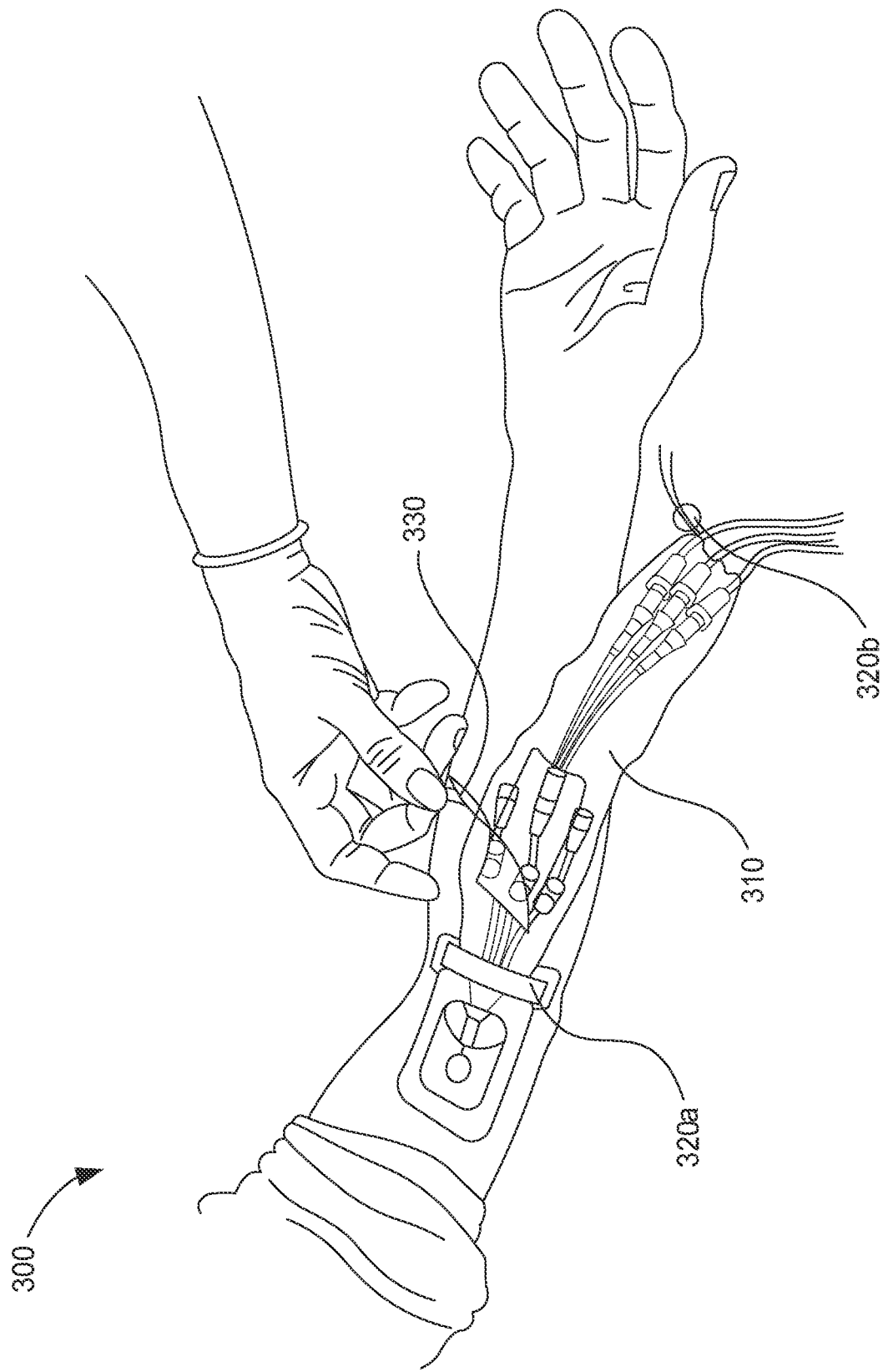
FIGS. 3A and 3B are illustrations of an encasement with a flap for protection of one or more lines from contaminants, according to an embodiment.
Figure 3B:
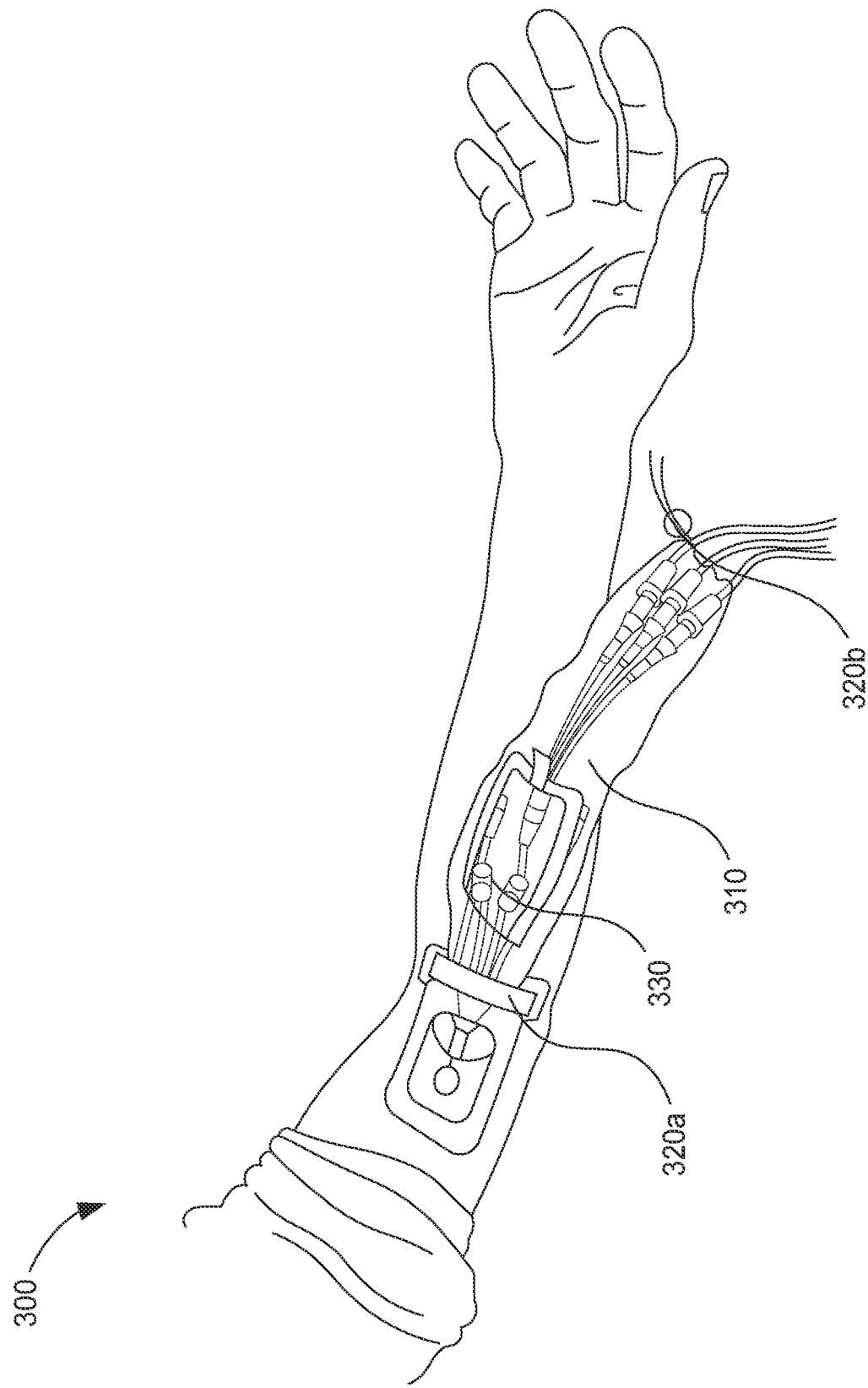

FIGS. 3A and 3B are illustrations of an encasement device 300 with a flap for protection of one or more lines or tubing (e.g., central lines) from contaminants, according to an embodiment. As shown, the encasement device 300 includes a sleeve 310 with a proximal closing element 320a, a distal closing element 320b (collectively referred to as closing elements 320), and a flap 330. As shown, the flap 330 includes a tab 331. In some embodiments, the sleeve 310, the proximal closing element 320a, and the distal closing element 320b can be the same or substantially similar to the sleeve 210, the proximal closing element 220a, and the distal closing element 220b, as described above with reference to FIG. 2. Thus, certain aspects of the sleeve 310, the proximal closing element 320a, and the distal closing element 320b are not described in greater detail herein.

The flap 330 can provide access to the lines and/or connectors along the lines (e.g., ports, Luer connectors, etc.) without removing the sleeve 310. The flap 330 is in an open position as shown in FIG. 3A and a closed position as shown in FIG. 3B. As shown, the tab 331 allows for ease of opening of the flap 330. In some embodiments, the flap 330 can include a resealable surface on the underside of the flap 330. In some embodiments, the resealable surface on the underside of the flap 330 can adhere to the outer surface of the sleeve 310. In some embodiments, the outer surface of the sleeve 310 can include a resealable surface to mate with the resealable surface on the underside of the flap 330. In some embodiments, the flap 330 can have a larger area than the area of the opening created by the removal of the flap 330, such that the flap 330 can cover more than the area of the opening. In some embodiments, the flap 330 can have length (i.e., a dimension in the longitudinal direction of the sleeve 310) of about 1 cm, about 2 cm, about 3 cm, about 4 cm, about 5 cm, about 6 cm, about 7 cm, about 8 cm, about 9 cm, about 10 cm, about 15 cm, about 20 cm, about 25 cm, or about 30 cm, inclusive of all values and ranges therebetween. In some embodiments, the flap 330 can have a width (e.g., a dimension in the lateral direction of the sleeve 310) of about 1 cm, about 2 cm, about 3 cm, about 4 cm, about 5 cm, about 6 cm, about 7 cm, about 8 cm, about 9 cm, or about 10 cm, inclusive of all values and ranges therebetween.

In some embodiments, the flap 330 can be disposed, such that the proximal end of the flap 330 is at least about 1 cm, at least about 2 cm, at least about 3 cm, at least about 4 cm, at least about 5 cm, at least about 6 cm, at least about 7 cm, at least about 8 cm, at least about 9 cm, at least about 10 cm, at least about 15 cm, at least about 20 cm, or at least about 25 cm from the proximal closing element 320a. In some embodiments, the flap 330 can be disposed, such that the proximal end of the flap 330 is no more than about 30 cm, no more than about 25 cm, no more than about 20 cm, no more than about 15 cm, no more than about 10 cm, no more than about 9 cm, no more than about 8 cm, no more than about 8 cm, no more than about 8 cm, no more than about 8 cm, no more than about 7 cm, no more than about 6 cm, no more than about 5 cm, no more than about 4 cm, no more than about 3 cm, or no more than about 2 cm from the proximal closing element 320a. Combinations of the above-referenced distances are also possible (e.g., at least about 1 cm and no more than about 30 cm or at least about 3 cm and no more than about 10 cm), inclusive of all values and ranges therebetween. In some embodiments, the flap 330 can be disposed, such that the proximal end of the flap 330 is about 1 cm, about 2 cm, about 3 cm, about 4 cm, about 5 cm, about 6 cm, about 7 cm, about 8 cm, about 9 cm, about 10 cm, about 15 cm, about 20 cm, about 25 cm, or about 30 cm from the proximal closing element 320a.

In some embodiments, the tab 331 can have a length suitable for a healthcare worker or a patient to hold by hand (e.g., via a thumb and index finger) and pull away to access the central lines. In some embodiments, the tab 331 can have a length of about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm, about 5 cm, about 6 cm, about 7 cm, about 8 cm, about 9 cm, or about 10 cm, inclusive of all values and ranges therebetween.

FIG. 4 is an illustration of an encasement device 400 for protection of one or more lines or tubing (e.g., central lines) from contaminants, according to an embodiment. As shown, the encasement device 400 includes a sleeve 410 with a distal closed end 412 and a proximal closing element 420a. In some embodiments, the sleeve 410 and the proximal closing element 420a can be the same or substantially similar to the sleeve 210 and the closing element 220a, as described above with reference to FIG. 2. Thus, certain aspects of the sleeve 410 and the proximal closing element 420a are not described in greater detail herein.

As shown, the closed end 412 is permanently closed. In other words, the sleeve 410 is configured as a bag, with one open end and one closed end. The sleeve 410 with the closed end 412 can be of particular use when the patient is not receiving treatment via the lines but still needs to be protected from infections between treatments.

FIG. 5 is an illustration of an encasement device 500 for protection of one or more lines or tubing (e.g., central lines) from contaminants, according to an embodiment. As shown, the encasement device 500 includes a sleeve 510 with a distal closed end 512 and a proximal closing element 520a, as well as a flap 530. In some embodiments, the sleeve 510, the closed end 512, and the proximal closing element 520a can be the same or substantially similar to the sleeve 410, the closed end 412, and the proximal closing element 420a, as described above with reference to FIG. 4. In some embodiments, the flap 530 and the tab 531 can be the same or substantially similar to the flap 330 and the tab 331, as described above with reference to FIGS. 3A and 3B. Thus, certain aspects of the sleeve 510, the terminal end 512, the proximal closing element 520a, the flap 530, and the tab 531 are not described in greater detail herein.

Inclusion of the closed end 512 with the tab 530 can protect the central lines during non-use while allowing access to the central lines. In some embodiments, intermittent IV fluid infusion, hemodialysis treatment, or intravenous push of medication can be given via an entrance through the opening of the sleeve 520 via the tab 530.

Figure 10:
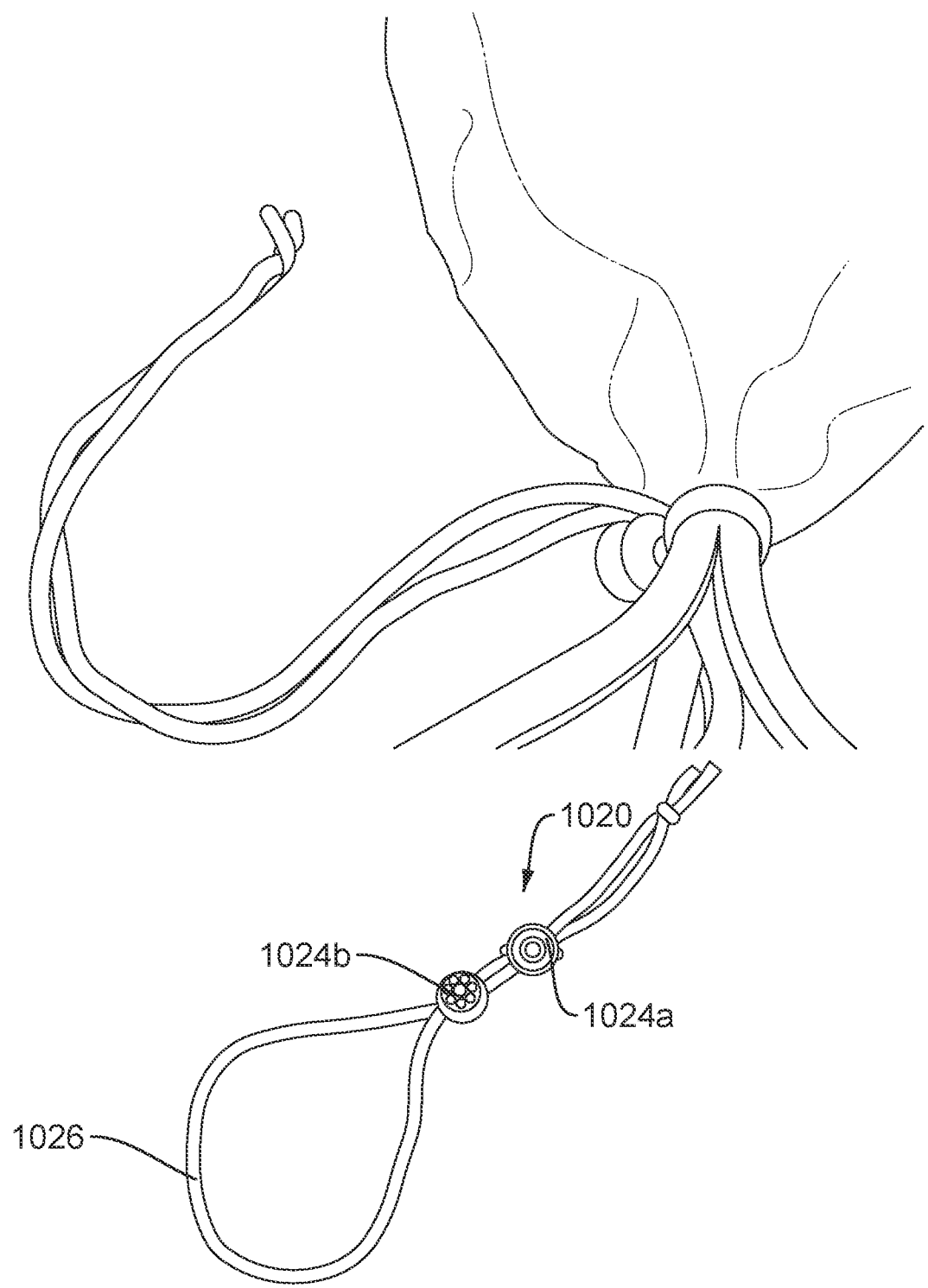
FIG. 10 is an illustration of a closing element of an encasement, according to an embodiment.

FIG. 10 is an illustration of an example closing element 1020, and its implementation in a sleeve, according to an embodiment. As shown, the closing element 1020 includes stopper snaps 1024a, 1024b (collectively referred to as stopper snaps 1024) and an elastic cord 1026. In some embodiments, the closing element 1020 can be the same or substantially similar to the closing element 120, as described above with reference to FIG. 1. Thus, certain aspects of the closing element 1020 are not described in greater detail herein.

As shown, the closing element 1020 includes two stopper snaps 1024. In some embodiments, the stopper snap 1024a can provide an anchor while the stopper snap 1024b can move along the elastic cord 1026 to tighten and loosen the grip of the elastic cord 1026 over the central lines. In some embodiments, the elastic cord 1026 can be partially disposed in a tunnel or channel at a terminal end of the sleeve during use. In some embodiments, the closing element 1020 can include 1, 2, 3, 4, 5, 6, 7, 8, 9, 10, or at least about 10 stopper snaps 1024, inclusive of all values and ranges therebetween.

Figure 11:
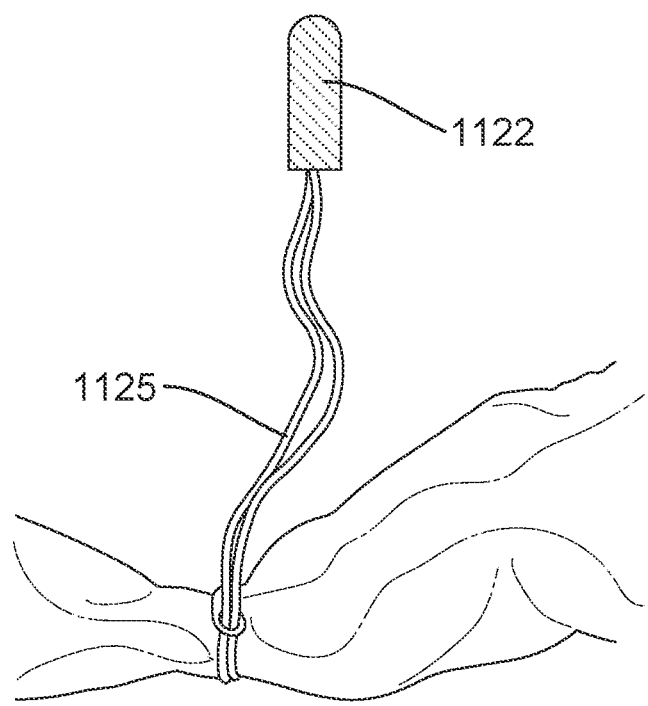
FIG. 11 is an illustration of a mounting loop of an encasement, according to an embodiment.

FIG. 11 is an illustration of an example mounting loop 1125 of an encasement device, according to an embodiment. As shown, the mounting loop 1125 includes a mounting strip 1122. The mounting strip 1122 can attach a terminal end of the mounting loop 1125 to a desired location (e.g., walls, furniture, patient bed, etc.). In some embodiments, the mounting strip 1122 can include an adhesive surface disposed thereon. In some embodiments, a strip of material can be removed from the mounting strip 1122 to expose the adhesive surface. In some embodiments, the adhesive surface of the mounting strip 1122 can be reusable, such that the mounting strip 1122 can be removed and re-attached. In some embodiments, the mounting loop 1125 can be incorporated into a closing element (e.g., closing element 120 or any of the other closing elements described herein). In other words, a closing element can close an end of the sleeve with the mounting strip 1122 attached to a portion (e.g., terminal end) of the closing element.

FIGS. 12A-12C are illustrations of encasement devices for protection of one or more lines or tubing (e.g., central lines) from contaminants, according to various embodiments. FIG. 12A shows an encasement device 1200 with a sleeve 1210 and closing elements 1220a, 1220b. As shown, the closing element 1220a includes an adhesive flange for coupling to a dressing, while the closing element 1220b includes a drawstring or cinch. FIG. 12B shows an encasement device 1200' mounted to a wall to show details of the dressing and the central lines running through the encasement device 1200'. The encasement device 1200' can include a closing element 1220a' including an adhesive strip and/or flange configured to secure to the dressing. FIG. 12C shows an encasement device 1200" mounted directly to a patient's arm, with a closing element 1220a' at a proximal end implemented as a flange and a closing element 1220b' at a distal end of the encasement in a closed position (and the central lines contained within the encasement device 1200").

Figure 13A:
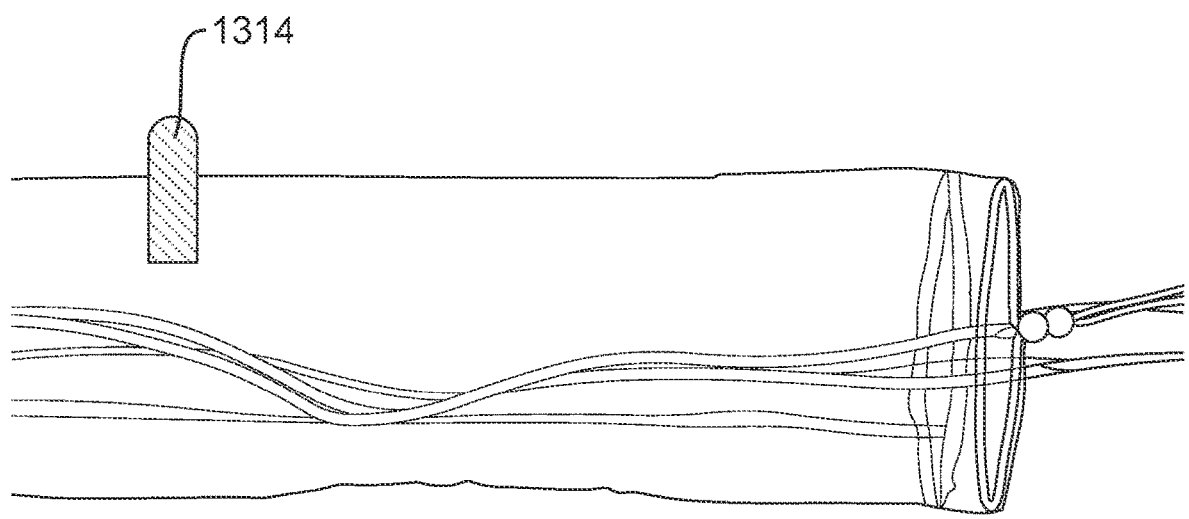
FIGS. 13A and 13B are illustrations of an encasement with adhesive strips for securement to surfaces, according to various embodiments.
Figure 13B:
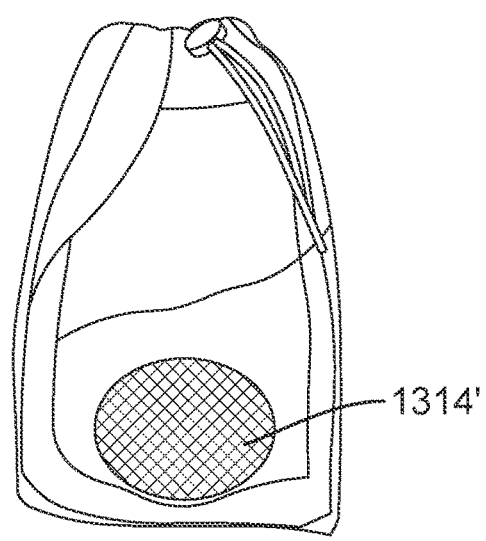

FIGS. 13A and 13B are illustrations of encasement devices with adhesive elements for securement to surfaces, according to various embodiments. The adhesive elements can be examples of coupling elements, as described with reference to FIG. 1. As shown, the encasement device in FIG. 13A includes an encasement or sleeve with an adhesive strip 1314 coupled directly to the surface of the sleeve. The adhesive strip 1314 can allow the sleeve to be coupled directly to a desired location (e.g., walls, furniture, patient bed, etc.). In some embodiments, the adhesive strip 1314 can be reusable such that it can be re-applied after becoming detached from a surface. In some embodiments, the adhesive strip 1314 can include a portion that can be removed to expose the adhesive surface. FIG. 13B is an illustration of an encasement with an adhesive element 1314' coupled directly to the sleeve. As shown, the adhesive element 1314' has a round shape. In some embodiments, the adhesive element 1314' can include a portion that can be removed to expose the adhesive surface.

Figure 14:
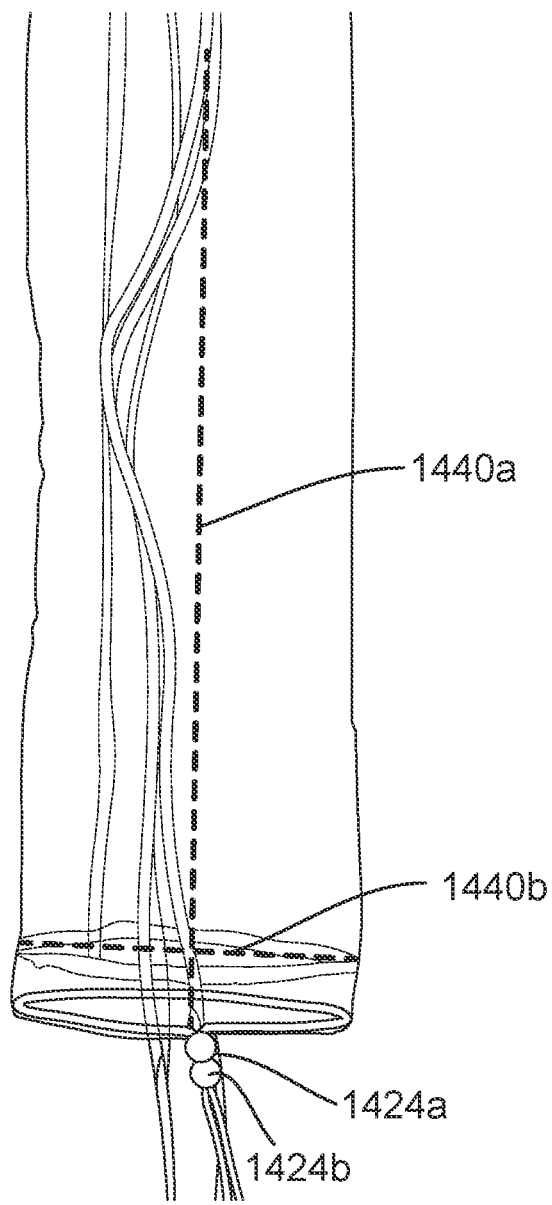
FIG. 14 is an illustration of an encasement with perforations, according to an embodiment.

FIG. 14 is an illustration of an encasement device with perforations, according to an embodiment. As shown, the encasement device includes a longitudinal perforation 1440a and a circumferential perforation 1440b. The perforations 1440a, 1440b and other components of the encasement device as depicted in FIG. 14 can be structurally and/or functionally similar to other perforations (e.g., perforation 140) and components, as described herein. The longitudinal perforation 1440a extends to at least one end (e.g., the proximal end) of the sleeve. In some embodiments, the longitudinal perforation 1440a extends the entire length of the sleeve, from one terminal end to another terminal end, so the sleeve can be quickly opened and/or removed. In some embodiments, the longitudinal perforation 1440a can extend to a location near the proximal end of the sleeve, e.g., distal to it by about 1 cm, about 2 cm, about 3 cm, about 4 cm, about 5 cm, about 6 cm, about 7 cm, about 8 cm, about 9 cm, about 10 cm, inclusive of all values and ranges therebetween. As shown, the circumferential perforation 1440b can extend around the entire circumference of the sleeve. In some embodiments, the circumferential perforation 1440b can extend around about 40%, about 50%, about 60%, about 70%, about 80%, or about 90% of the circumference of the sleeve, inclusive of all values and ranges therebetween. In use, a healthcare professional can open the sleeve along the longitudinal perforation 1440a and/or detach a closing element including stopper snaps 1424a, 1424b from the sleeve via circumferential perforation 1440b. Removal of the closing element from the sleeve and perforating along a length of the sleeve can enable a user to remove the sleeve from being around one or more lines that are within a patient.

Figure 15A:
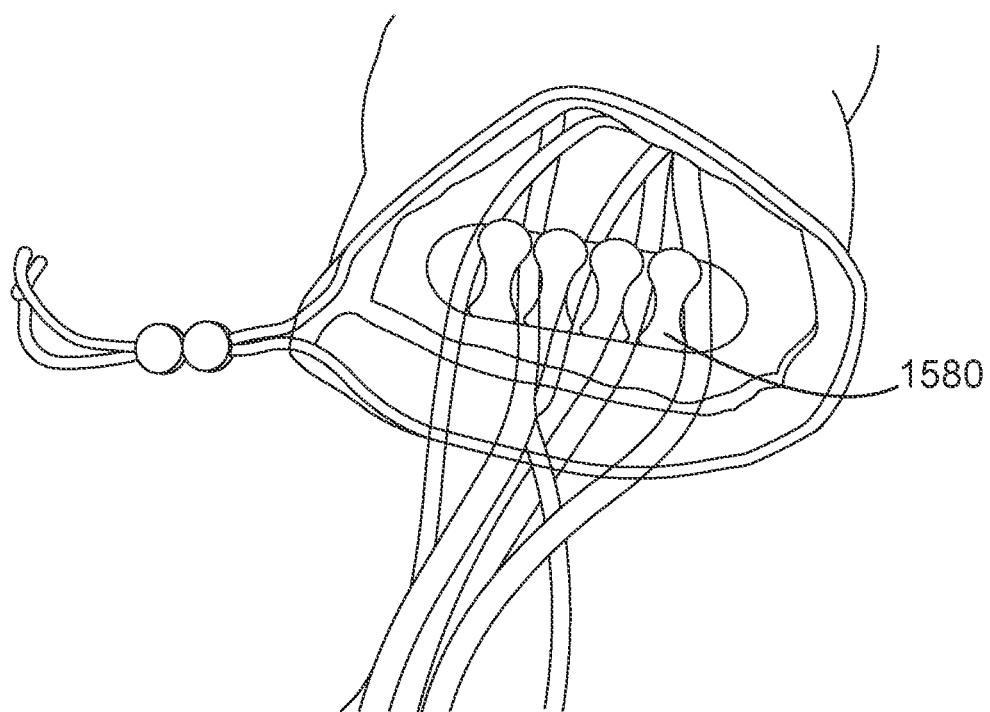
FIGS. 15A and 15B are illustrations of encasements with holders, according to various embodiments.
Figure 15B:
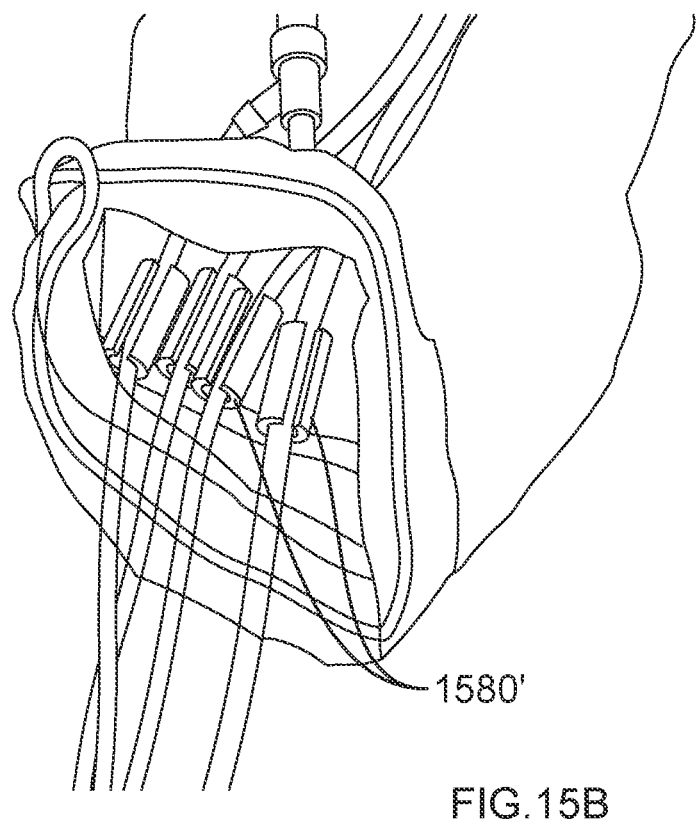

FIGS. 15A and 15B are illustrations of encasement devices with holders, according to various embodiments. FIG. 15A includes a holder 1580 with five IV tubes secured therein. In other words, the holder 1580 includes securements for five IV tubes. In some embodiments, the holder 1580 can include securements for 1, 2, 3, 4, 6, 7, 8, 9, 10, or more than about 10 IV tubes. As shown, the holder 1580 includes rounded cavities for insertion and securement of central lines. In some embodiments, the holder 1580 can be secured directly to the interior of the sleeve. In some embodiments, the holder 1580 can be detached from the interior of the sleeve. FIG. 15B includes a holder 1580' with four IV tubes secured into clips on the holder 1580.' In some embodiments, the holder 1500' can be attached to the interior of the sleeve. In some embodiments, the holder 1580' can be detached from the interior of the sleeve. The holders 1580, 1580' can be structurally and/or functionally similar to other holders described herein, including holder(s) 180 as described with respect to FIG. 1.

Figure 16:
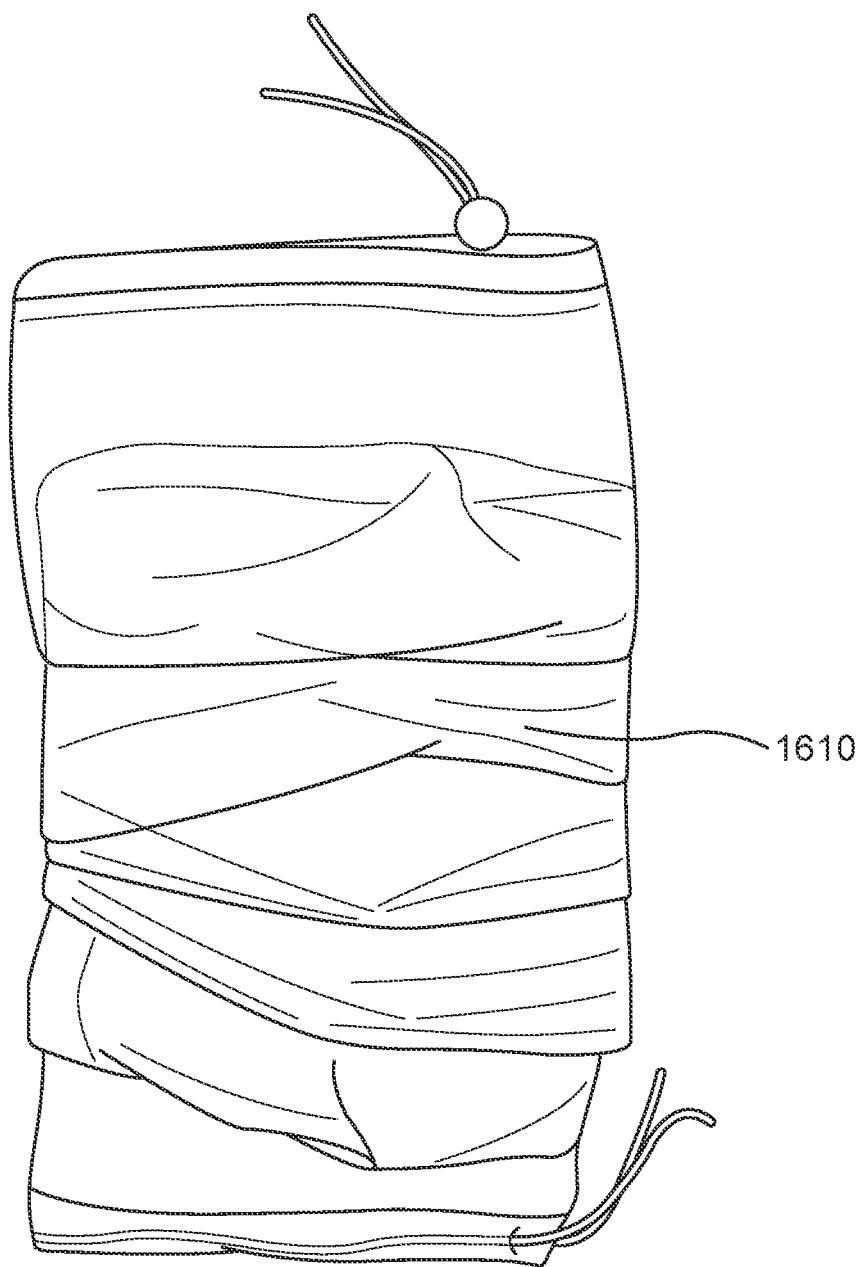
FIG. 16 is an illustration of an encasement in a collapsed and folded configuration, according to an embodiment.

The encasement devices as described herein can be packed in individual packs. Together these packs can form a kit. For compact storage, the sleeves described herein can be collapsed and/or folded. FIG. 16 is an illustration of a sleeve 1610 in a collapsed or folded configuration, according to an embodiment. As shown, the sleeve 1610 is folded in a repeating concentric pushed-in pattern. In other words, a first portion of the sleeve 1610 can be folded into the inside of a second portion of the sleeve 1610, and the second portion of the sleeve can be folded into the inside of a third potion of the sleeve, and so on. Said another way, the sleeve 1610 is collapsed into itself via a series of Z-shaped folds. The collapsed configuration can be useful for storage or transport of the sleeve 1610. In some embodiments, the sleeve 1610 can more easily be placed into a package (e.g., packs 650, as described below with reference to FIGS. 6A and 6B) in its collapsed state. The collapsing can reduce the effective length of the sleeve 1610 during storage or transport by a factor of at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1,000.

FIGS. 6A and 6B are illustrations of a set of packs 650 for packaging of encasement devices, according to an embodiment. As shown, FIG. 6A is a side view of five packs 650 hanging from an IV pole IVP, while FIG. 6B is a front view of the packs 650 hanging from the IV pole IVP. Each pack 650 can include one encasement device, and the packs 650 can be arranged vertically on a single strip, with each of the packs 650 attached to a strip S. The strip S can be a tear away strip. In some embodiments, the packs 650 can be attached to the strip S via an adhesive. In some embodiments, the adhesive can be resealable. As shown, the strip S includes 5 packs 650. In some embodiments, the strip S can include 1, 2, 3, 4, 6, 7, 8, 9, 10, 11, 12, 13, 14, 15, 16, 17, 18, 19, 20, or more than 20 packs 650, inclusive of all values and ranges therebetween. In some embodiments, the packs 650 can include a tab disposed thereon for ease of opening. In some embodiments, the packs 650 can be composed of a material that can be torn open by hand. In some embodiments, multiple encasement devices can be disposed in each of the packs 650. In some embodiments, the packs 650 can include polybag materials (e.g., LDPE, LLDPE, MDPE, PP, PLA), foil, lined materials (i.e., materials having an outer layer and an inner lining), barrier pouches, cellulose packaging, or any other suitable materials or combinations thereof. In some embodiments, the packs 650 can include plastic encasements (e.g., hard plastic encasements), PP, HDPE, polybags inside a paperboard or cellulose and/or fiber-based container, or combinations thereof.

Figure 7B:
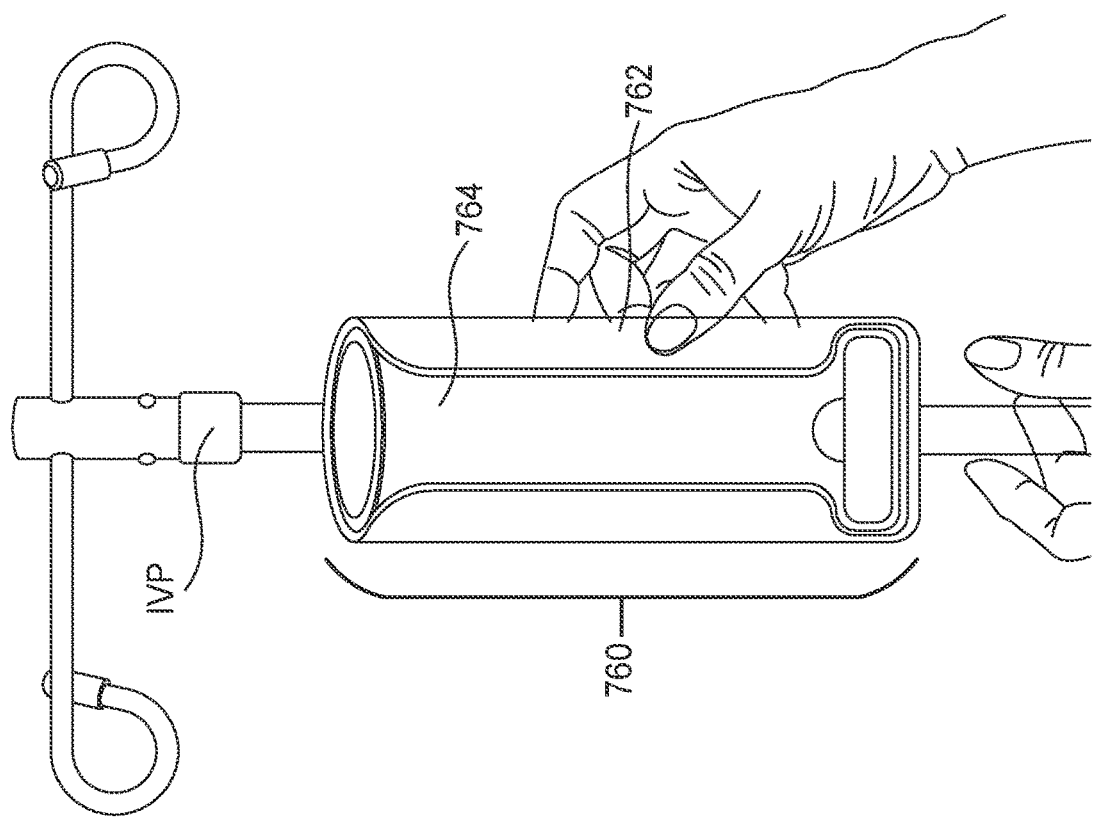
FIGS. 7A and 7B are illustrations of a system for dispensation of encasement packs, according to an embodiment.
Figure 7A:
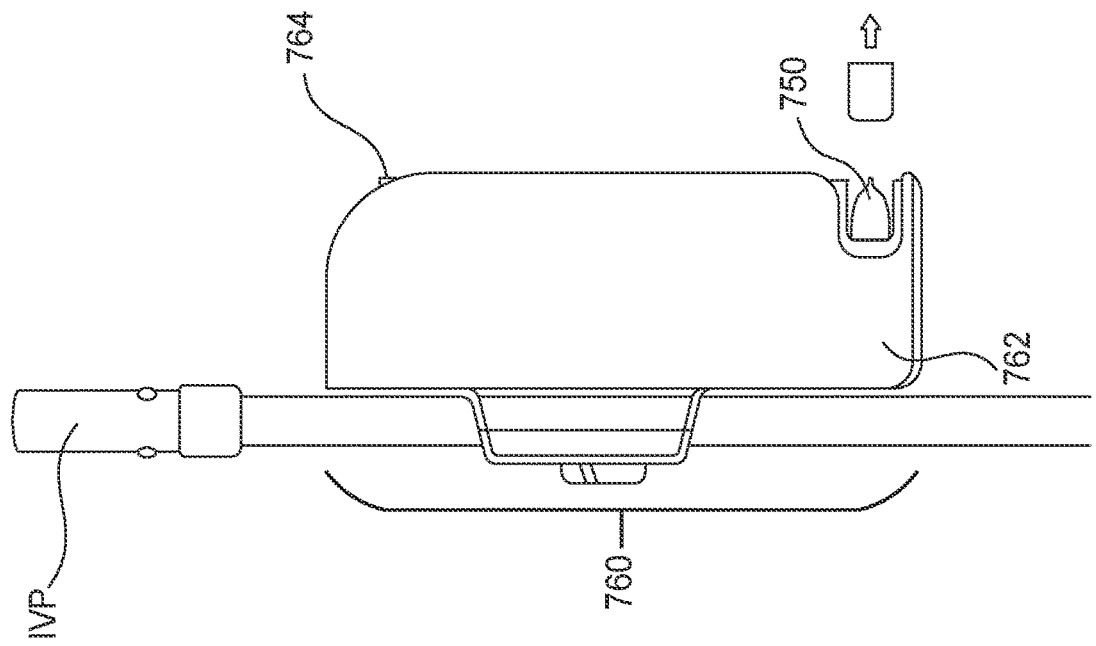

In some embodiments, a dispenser can be used to dispense one or more packs including encasement devices described herein. FIGS. 7A and 7B are illustrations of a system for dispensing of encasement packs 750, according to an embodiment. As shown, the packs 750 are disposed in a dispenser 760. The dispenser 760 includes a casing 762 and a box 764 and is suspended from an IV pole IVP. FIG. 7A is a side view of the system while FIG. 7B is a front view of the system. In some embodiments, the packs 750 can be the same or substantially similar to the packs 650, as described above with reference to FIGS. 6A-6B. Thus, certain aspects of the packs 750 are not described in greater detail herein.

As shown, the box 764 fits in the casing 762 and can be opened to dispense the packs 750. As shown, the packs 750 are arranged in a stacked configuration in the box 764. As shown, the box has a removable section that can be removed from the front to gain access to the packs 750. In some embodiments, the box 764 can be composed of cardboard, corrugated cardboard, or any other material that can be perforated, such that a section can be removed to access the packs 750. In some embodiments, the casing 762 can be composed of a polymer, a plastic, an injected molded plastic, or any other suitable material or combinations thereof. In some embodiments, the dispenser 760 can be sized to hold about 2, about 3, about 4, about 5, about 6, about 7, about 8, about 9, about 10, about 11, about 12, about 13, about 14, about 15, about 16, about 17, about 18, about 19, or about 20 packs 760, inclusive of all values and ranges therebetween. In some embodiments, the box 764 may be omitted or removed prior to the packs 750 being placed within the dispenser 760. As such, the individual packs 750 can be placed directly within the dispenser 760 without the presence of a box. While a box 764 is described, it can be appreciated that any other type of enclosure or housing can be used to contain one or more packs 750, including, for example, flexible containers such as bags, meshes, etc. In some embodiments, the box 764 can include a paperboard tube of individually wrapped sleeves (i.e., wrapped in the packs 750). In some embodiments, the box 764 can be replaced once all of the sleeves in the packs 750 are consumed.

Figure 8A:
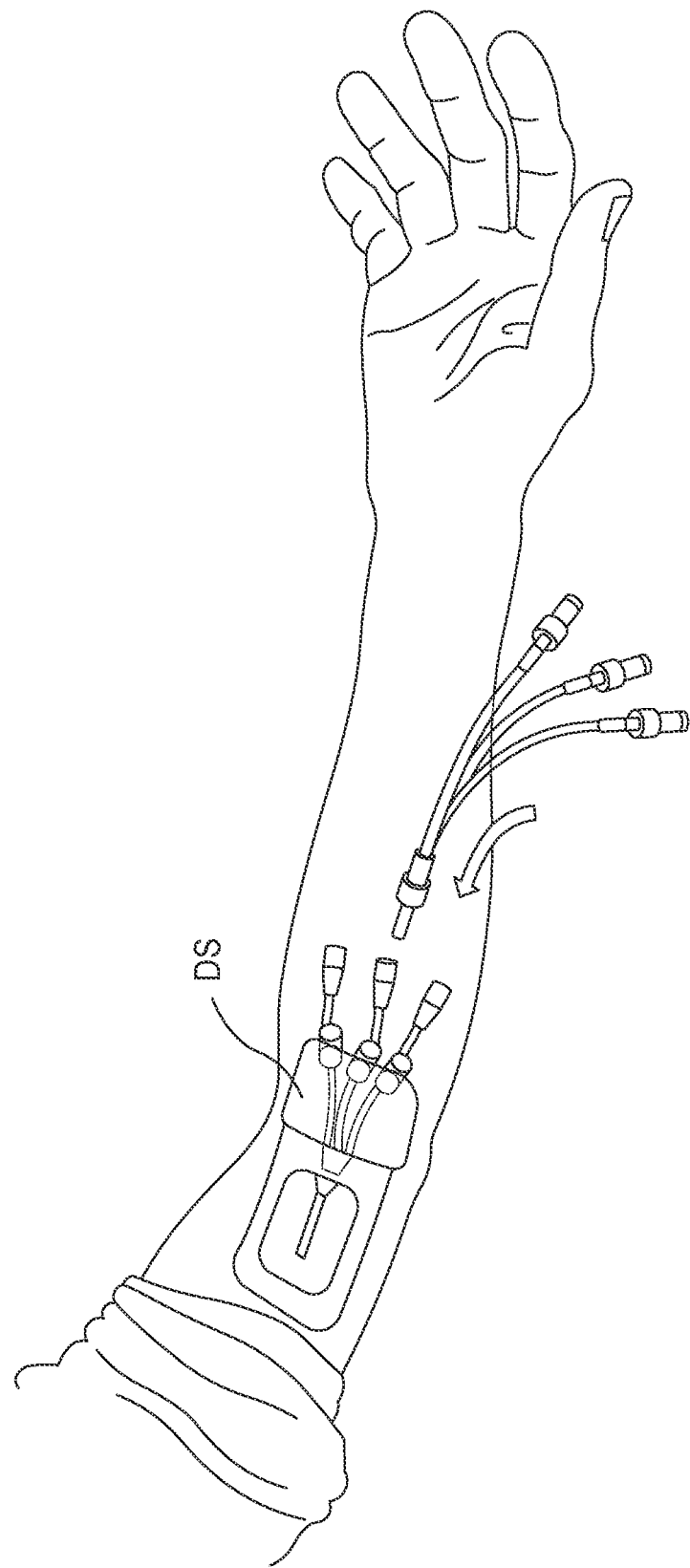
Figure 8B:
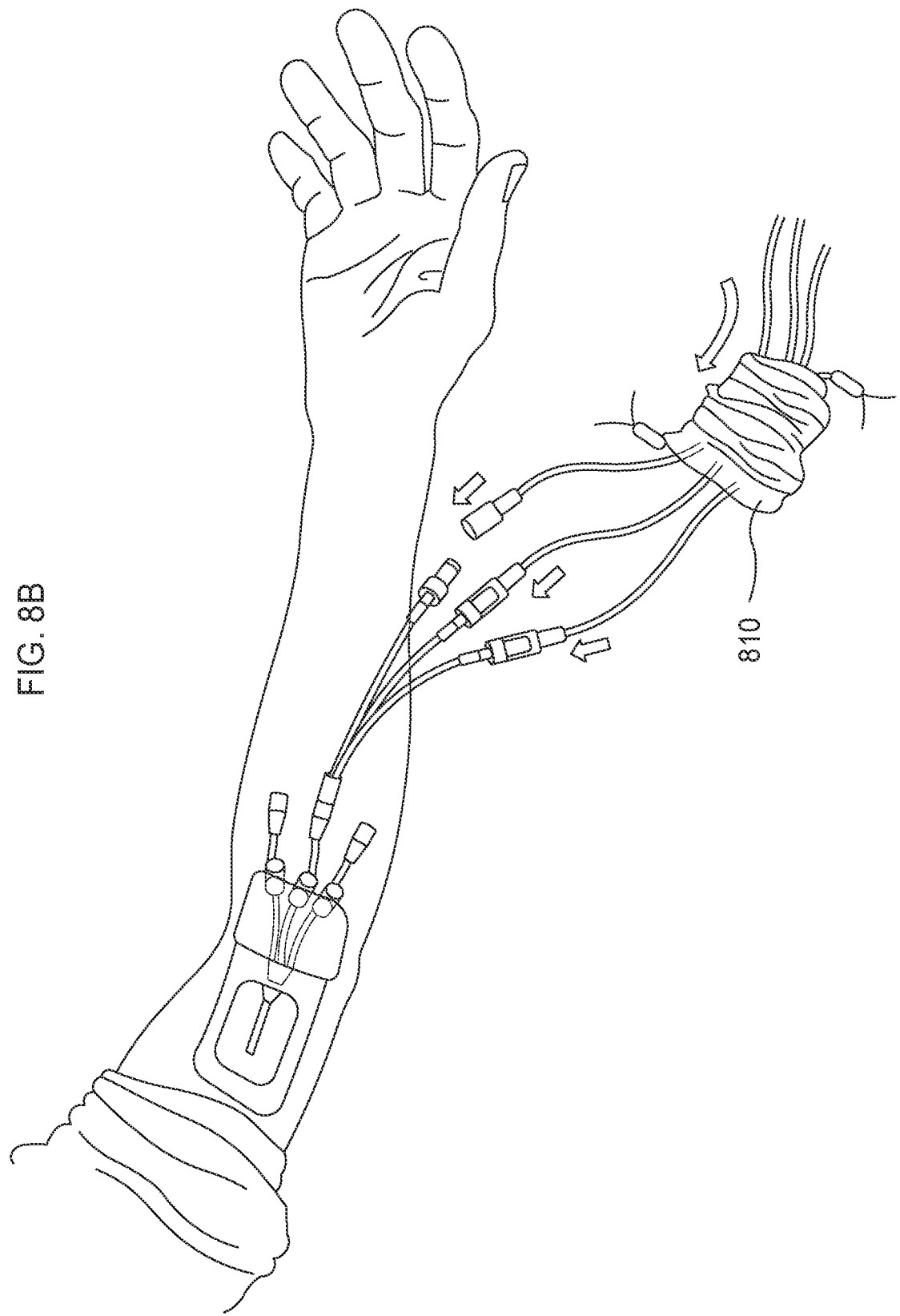
Figure 8D:
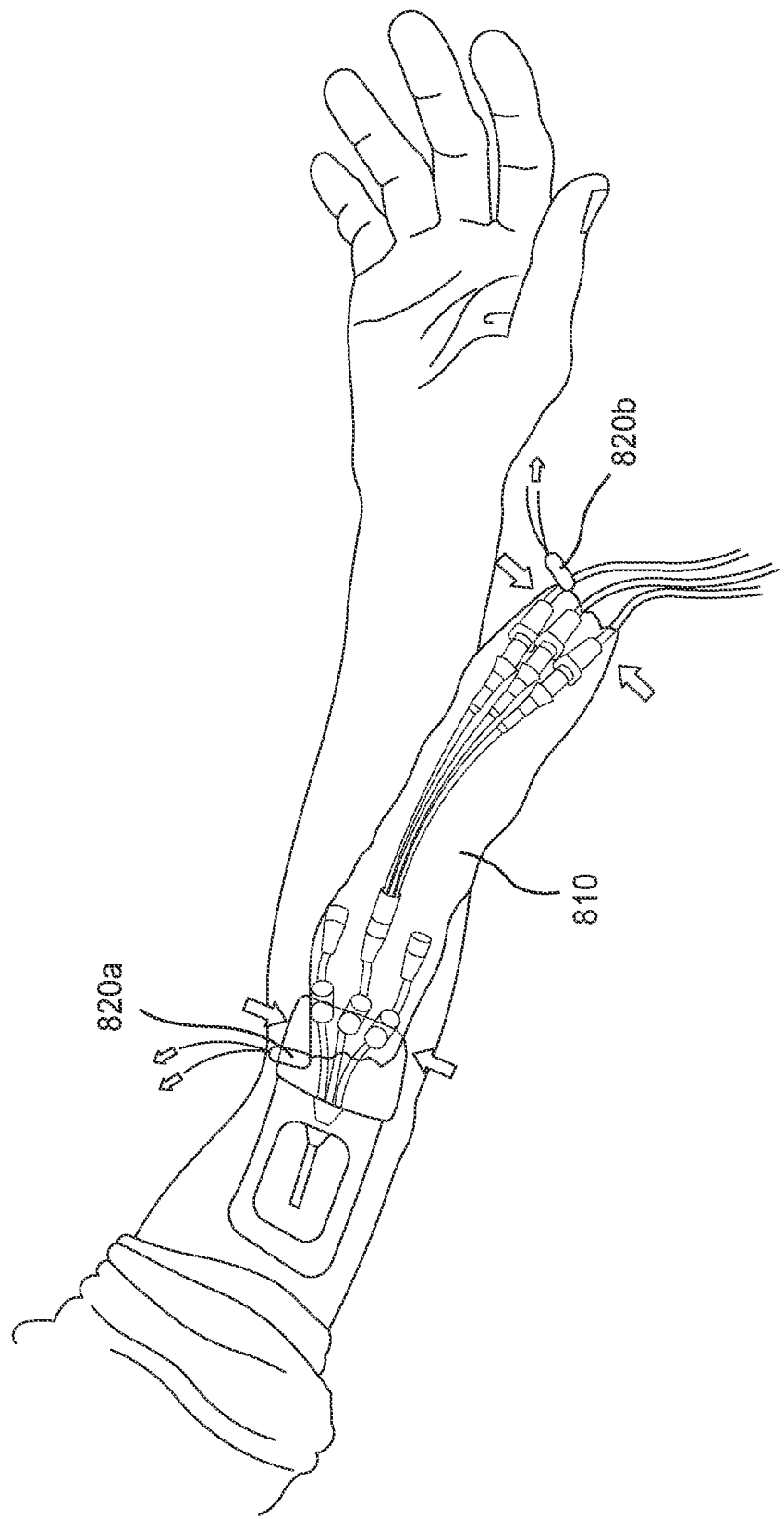
Figure 8E:
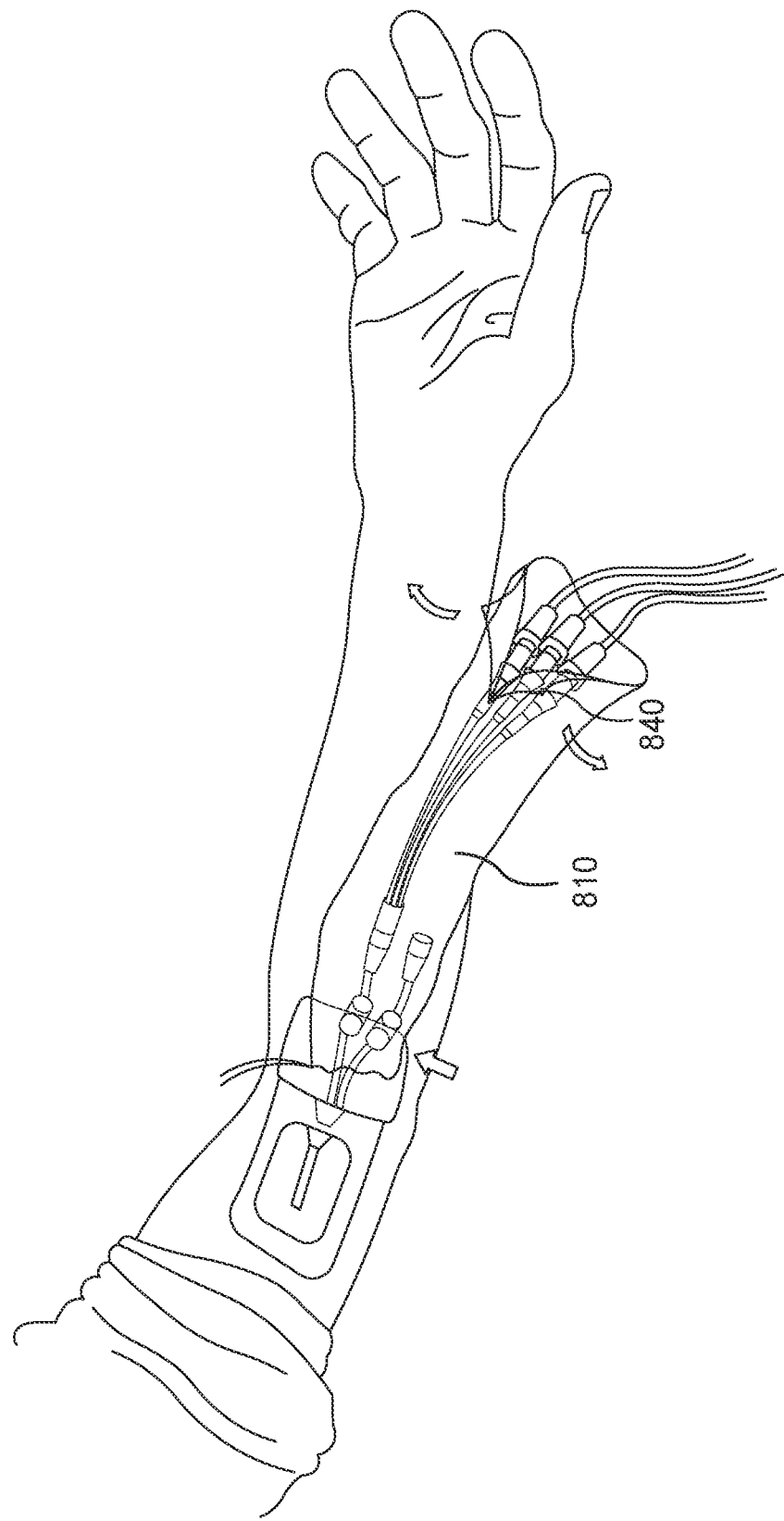

FIGS. 8A-8E are illustrations of a method of deploying an encasement device to protect IV lines from contaminants, according to various embodiments. As shown, the method includes attaching a central line connection to an IV line connection port in FIG. 8A. FIG. 8B shows the feeding of IV lines through a sleeve 810. The sleeve 810 can include components that are functionally and/or structurally similar to other sleeves described herein. FIG. 8C shows an extension of the sleeve 810 over IV line access ports and to a dressing DS. FIG. 8D shows securement of the sleeve 810 over a first region along the central lines near the dressing and over a second region along the IV lines and distal to the first region. The sleeve 810 can have two closing elements 820a, 820b, which can be configured to close around the central lines and/or IV line(s) at the first and second regions. In an embodiment, the closing elements can be implemented as snap-fit buttons. FIG. 8E shows removal of the sleeve 810 from the central lines and IV lines via tearing along perforations 840.

Figure 8G:
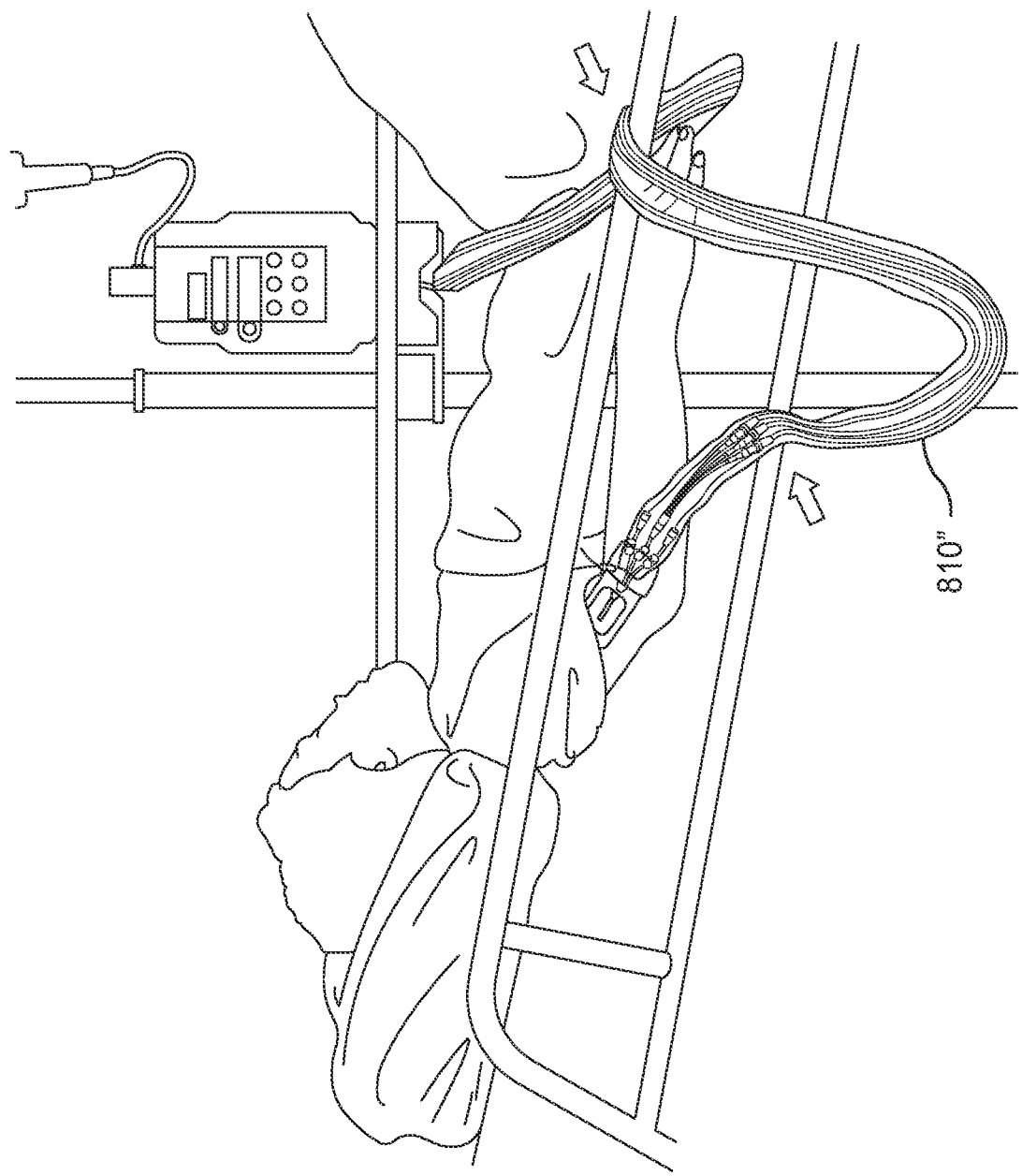

FIG. 8F shows extension of a long sleeve 810' along the length of the IV lines and central lines. The sleeve 810' can be a longer version of the sleeve 810 depicted with respect to FIGS. 8A-8E and can be deployed in a similar manner to sleeve 810. The sleeve 810', however, has a longer length and therefore can cover lines having longer length. FIG. 8G shows a patient with a sleeve 810" employed, with a proximal end of the sleeve 810" cinched near the dressing and a distal end of the sleeve coupled closest to an IV pump. The sleeve 810' can be a longer version of the sleeve 810 depicted with respect to FIGS. 8A-8E and can be deployed in a similar manner to sleeve 810. The sleeve 810', however, has a length that can extend from the dressing to the IV pump.

While FIGS. 8A-8G are described with reference to a central line, it can be appreciated that the sleeves 810, 810', 810" can be used with other types of lines or tubing, including peripheral lines, IV lines, arterial lines, etc.

FIG. 9 is a block diagram of a method 900 of deploying an encasement device (e.g., such as any of the encasement devices or sleeves described herein) to protect a central line from contaminants, according to an embodiment. As shown, the method 900 optionally includes connecting an IV line extension to a central line port, at 901. The method 900 further includes feeding a terminal end of one or more IV lines through the sleeve, at 902, coupling the terminal ends of the IV line to the central line port, at 903, extending the sleeve over the central lines and central line ports and over at least a portion of the IV lines, at 904, and securing the first terminal end of the sleeve, at 905. The method 900 optionally includes securing a second terminal end of the sleeve, at 906, accessing the central line and/or IV line(s) and/or ports, at 907, and removing the sleeve, at 908.

At 901, an IV line extension is optionally connected to a central line port. The central line port can come from a dressing, and the IV extension piece can allow for multiple IV lines to be fed to a single central line port in the patient's body. At 902, a terminal end of the IV line is fed through a sleeve (e.g., the sleeve 110, as described above with reference to FIG. 1). In some embodiments, the sleeve can be compressed or bunched together as the central line(s) is/are fed through the sleeve. In some embodiments, the sleeve can be fully extended as the IV line(s) is/are fed through the sleeve.

The terminal end of the IV line is coupled to the central line port, at 903. In some embodiments, if the IV extension piece was connected to the central line port at 901, 903 can include coupling the central lines to the IV extension piece. The coupling at 903 can establish a fluidic pathway from a source (e.g., an IV bag, pump, or other device) to a patient's body. At 904, the sleeve extends over at least a portion of the central line(s) that is not covered by the central line dressing, and extends over at least a portion of the IV line. This extension protects multiple points along the IV line(s) that would otherwise be susceptible to contamination. In some embodiments, the extension can extend from the dressing to an IV pump. In some embodiments, the extension at the proximal end can go to the dressing. In some embodiments, the extension at the proximal end can go to a location near the dressing, e.g., a location distal to the dressing by a distance of about 1 cm, about 2 cm, about 3 cm, about 4 cm, about 5 cm, about 6 cm, about 7 cm, about 8 cm, about 9 cm, or about 10 cm, inclusive of all values and ranges therebetween. In some embodiments, the distal end of the sleeve can extend to a location distal to each connection point along the IV lines. In some embodiments, the distal end of the sleeve can extend to the IV pump. In some embodiments, the distal end of the sleeve can extend to a location proximal to the IV pump by about 1 cm, about 2 cm, about 3 cm, about 4 cm, about 5 cm, about 6 cm, about 7 cm, about 8 cm, about 9 cm, about 10 cm, about 20 cm, about 30 cm, about 40 cm, about 50 cm, about 60 cm, about 70 cm, about 80 cm, about 90 cm, about 1 m, about 2 m, about 3 m, about 4 m, about 5 m, about 6 m, about 7 m, about 8 m, about 9 m, or about 10 m, inclusive of all values and ranges therebetween.

A first terminal end of the sleeve is secured, at 905. In some embodiments, the first terminal end of the sleeve can be the proximal end of the sleeve. In some embodiments, the first terminal end of the sleeve can be secured to the dressing. In some embodiments, the first terminal end of the sleeve can be secured to a location near the dressing (e.g., around the outside of the IV lines at a location distal to but near the dressing). In some embodiments, the coupling of the first terminal end can be via an adhesive, a drawstring, a cinch, an adhesive flange, and/or any of the other mechanisms described above with reference to the closing elements 120, described with reference to FIG. 1.

The second terminal end of the sleeve is optionally secured, at 906. In some embodiments, the second terminal end of the sleeve can be the distal end of the sleeve. In some embodiments, the second terminal end of the sleeve can be secured to an IV pump. In some embodiments, the second terminal end of the sleeve can be secured to a location proximal to the IV pump (e.g., around the outside of the IV at a location proximal to but near the IV pump), e.g., by about 1 cm, about 2 cm, about 3 cm, about 4 cm, about 5 cm, about 6 cm, about 7 cm, about 8 cm, about 9 cm, about 10 cm, about 20 cm, about 30 cm, about 40 cm, about 50 cm, about 60 cm, about 70 cm, about 80 cm, about 90 cm, about 1 m, about 2 m, about 3 m, about 4 m, about 5 m, about 6 m, about 7 m, about 8 m, about 9 m, or about 10 m, inclusive of all values and ranges therebetween. In some embodiments, securing the second terminal end of the sleeve can be via an adhesive, a drawstring, a cinch, an adhesive flange, and/or any of the other mechanisms described above with reference to the closing elements 120, described with reference to FIG. 1. In some embodiments, the second terminal end of the sleeve can be a closed end and therefore the second terminal end of the sleeve may not need to be secured.

The method 900 optionally includes accessing the central line and/or IV line and/or ports, at 907. In some embodiments, the central line can be accessed while the sleeve is covering the central line and IV line(s). For example, the central line and IV line(s) can be accessed through a flap in a sidewall of the sleeve. In some embodiments, the central line and IV line(s) can be accessed by opening one or more of the closing features (e.g., cinch). Opening one or more of the closing features can allow a medical professional to roll the sleeve out of the way to access the central line and IV line(s), and then roll the sleeve back into place to re-cover the central line and IV line(s).

The sleeve is optionally removed, at 908. In some embodiments, removal of the sleeve can be via tearing of one or more perforations along the length and/or perimeter of the sleeve. In some embodiments, the removal of the sleeve can be via unthreading the IV lines and pulling them through the sleeve and out of the sleeve.

While FIG. 9 is described with reference to a central line and IV line(s), it can be appreciated that method 900 can involve other types of lines or tubing, including peripheral lines, arterial lines, hemodialysis lines, etc.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, "proximal" and "distal" refer to locations relative to an entry point of a central line into the patient's body. For example, if point A is located on the central line, 5 cm from the entry point and point B is located on the central line, 10 cm from the entry point, then point A is proximal to point B and point B is distal to point A.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A device, comprising:
   a flexible sleeve sized to receive and enclose a set of one or more medical lines connected to a patient, the set of medical lines including a catheter disposed through an insertion site, the flexible sleeve having first and second ends and a flexible body extending between the first and second ends, the first end of the flexible sleeve defining an opening and the second end of the flexible sleeve with a closing element or being permanently closed;
   a flange disposed at the first end of the flexible sleeve, the flange surrounding the opening and having an adhesive surface,
   the adhesive surface configured to directly attach to a dressing or surface at the insertion site such that the flange encircles the catheter and the flexible sleeve closes around the set of medical lines,
   the adhesive surface further configured to detach from the dressing or surface in response to a peeling force applied by a user to the flange; and
   a flap disposed over a lateral opening formed in the flexible body between the first and second ends of the flexible sleeve, the flap configured to open to allow access to one or more connectors coupled to the catheter and disposed within the flexible sleeve when the adhesive surface is attached to the dressing.

2. The device of claim 1, wherein the flexible sleeve includes one or more antimicrobial agents disposed along a length of the flexible body, the one or more antimicrobial agents include at least one of: a bioactive metal, silver, copper, zinc, nickel, cobalt, molybdenum, an oligodynamic metal, a derived alloy of an oligodynamic metal, an ionized derivative of an oligodynamic metal, an organic antimicrobial, an organic moiety formed of one or more essential oils, an ionic polymer, an ionic oligomer, an ionic rubber, or an organometallic material.

3. The device of claim 1, wherein the flexible sleeve includes one or more antimicrobial agents embedded in the flexible sleeve.

4. The device of claim 1, wherein the flexible sleeve includes one or more antimicrobial agents that coat an inner surface and/or an outer surface of the flexible sleeve.

5. The device of claim 1, wherein the flexible sleeve includes one or more antimicrobial agents disposed along a length of the flexible body, the one or more antimicrobial agents including:
a first antimicrobial agent that is embedded in the flexible sleeve; and
a second antimicrobial agent that coats an inner surface or an outer surface of the flexible sleeve, the second antimicrobial agent being different from the first antimicrobial agent.

6. The device of claim 1, wherein the flexible sleeve has an optical transmittance of at least about 50%.

7. The device of claim 1, wherein the flexible sleeve is tinted with a prescribed color to indicate at least one of a type of the set of medical lines disposed therein or a characteristic of the patient.

8. The device of claim 1, wherein the first end of the flexible sleeve includes the closing element, the closing element including at least one of: a resealable adhesive element configured to adhere to a surface of the flexible sleeve to close around the set of medical lines or a drawstring configured to tighten to close around the set of medical lines and to secure the first end of the flexible sleeve relative to the set of medical lines.

9. The device of claim 1, further comprising:
a perforation line formed in the flexible sleeve and extending along a longitudinal length of the flexible sleeve, the perforation line configured to allow the flexible sleeve to be opened along the longitudinal length of the flexible sleeve such that the flexible sleeve can be removed from the set of medical lines.

10. The device of claim 9, wherein the perforation line is a first perforation line, the device further including:
a second perforation line extending circumferentially around the flexible sleeve, the second perforation line configured to allow a first portion of the flexible sleeve to separate from a second portion of the flexible sleeve.

11. The device of claim 9, wherein the flexible sleeve has a length of at least about 5 centimeters.

12. The device of claim 9, wherein the first end of the flexible sleeve includes the closing element, the closing element including at least one of: a resealable adhesive element configured to adhere to a surface of the flexible sleeve to close around the set of medical lines, or a drawstring configured to tighten to close around the set of medical lines and to secure the first or second end of the flexible sleeve relative to the set of medical lines.

13. The device of claim 1, further comprising a mechanical coupler or an adhesive disposed on an outside of the flexible sleeve, the mechanical coupler or the adhesive configured to extend between the flexible sleeve and a nearby structure or surface and to couple the flexible sleeve to the nearby structure or surface to mitigate medical line entanglement.

14. The device of claim 1, wherein the adhesive surface has a peel strength of between about 1 Newton/25 millimeters to about 25 Newtons/25 millimeters.

15. The device of claim 1, wherein the adhesive surface has an annular shape or a rectangular shape.

16. The device of claim 1, wherein the adhesive surface is resealable.

17. The device of claim 1, wherein the flexible sleeve is composed of at least one of:
a naturally derived biopolymer, a synthetically derived biopolymer, polylactic acid (PLA), polyhydroxyalkanoates (PHA), polyhydroxybutyrate (PHB), poly-(3-hydroxybutyrate-co-3-hydroxyhexanoate (PHBH), poly-(3-hydroxybutyrate-co-3-hydroxyvalerate (PHBV), polyvinyl alcohol (PVOH), polybutylene succinate (PBS), a rubber, or a copolymer.

18. A device, comprising:
a flexible sleeve sized to receive and enclose a set of medical lines connected to a patient, the flexible sleeve having first and second ends and a flexible body extending between the first and second ends, the set of medical lines including a catheter disposed through an insertion site and between the first and second ends and terminating in one or more connectors and one or more lines configured to couple to the one or more connectors, each of the first and second ends of the flexible sleeve defining an opening;
at least one closing element, the at least one closing element disposed at the first or second end of the flexible sleeve and configured to selectively open and close the opening of the first or second end,
the at least one closing element configured to open the opening of the first or second end of the flexible sleeve such that the flexible sleeve can be placed around the set of medical lines,
the at least one closing element configured to close the opening of the first or second end of the flexible sleeve around the set of medical lines at the first or second end of the flexible sleeve such that the flexible sleeve is configured to protect the set of medical lines from contaminants;
a flange disposed at the first end of the flexible sleeve, the flange surrounding the opening of the first end and having an adhesive surface,
the adhesive surface configured to directly attach to a dressing or surface at the insertion site such that the flange encircles the catheter and the flexible sleeve closes around the set of medical lines,
the adhesive surface further configured to detach from the dressing or surface in response to a peeling force applied by a user to the flange; and
a flap disposed over a lateral opening formed in the flexible body between the first and second ends of the flexible sleeve, the flap configured to open to allow access to the one or more connectors coupled to the catheter and disposed within the flexible sleeve when the adhesive surface is attached to the dressing.

19. The device of claim 18, wherein the flap includes a first portion that is attached to or integrally formed with the flexible body and a second portion having one or more resealable surfaces configured to reversibly couple to an exterior surface of the flexible body of the flexible sleeve.

20. The device of claim 18, wherein the flexible body has a resealable surface near the lateral opening that is configured to reversibly couple to the flap.

21. The device of claim 18, wherein the flap includes a tab configured to be pulled to open the flap.

22. The device of claim 18, wherein the flexible sleeve is sized to receive the set of medical lines including at least three lines, the device further comprising:
   at least one holder disposable within the flexible sleeve and configured to space the at least three lines from each other.

23. The device of claim 22, wherein the holder is disposed near the lateral opening of the flexible body.

24. The device of claim 18, wherein the first end of the flexible sleeve is disposed closer to an insertion site of the catheter, and the lateral opening is disposed at least about 1 centimeter from the first end of the flexible sleeve.

25. The device of claim 18, wherein the flap has a length of between about 5 centimeters and about 15 centimeters.

26. The device of claim 18, wherein the flexible sleeve includes one or more antimicrobial agents disposed throughout an entire length of the flexible body and the flap, the flap having an additional coating layer of the one or more antimicrobial agents disposed thereon.

* * * * *